United States Patent
Kriesel

(10) Patent No.: US 8,480,656 B2
(45) Date of Patent: Jul. 9, 2013

(54) TWO PART FLUID DISPENSER

(75) Inventor: Marshall S. Kriesel, St. Paul, MN (US)

(73) Assignee: BioQuiddity, Inc., San Francisco, CA (US)

( * ) Notice: Subject to any disclaimer, the term of this patent is extended or adjusted under 35 U.S.C. 154(b) by 1067 days.

(21) Appl. No.: 12/231,556

(22) Filed: Sep. 3, 2008

(65) Prior Publication Data

US 2010/0056996 A1    Mar. 4, 2010

(51) Int. Cl.
*A61K 9/22* (2006.01)

(52) U.S. Cl.
USPC ............ 604/891.1; 604/9; 604/134; 604/135; 604/136; 604/137; 604/138; 604/139; 604/140; 604/141; 604/142; 604/143; 604/151; 604/153; 604/156; 604/164.01; 604/164.02; 604/164.09; 604/30; 604/236; 604/537; 604/323; 222/207; 222/209; 222/213

(58) Field of Classification Search
USPC ............... 604/9, 890.1, 891.1, 134–143, 151, 604/153, 156, 164.02, 164.09, 30, 236, 537, 604/323; 222/207, 209, 213
See application file for complete search history.

(56) References Cited

U.S. PATENT DOCUMENTS

| | | | |
|---|---|---|---|
| 2,236,084 A | 3/1941 | Brown | |
| 3,568,889 A * | 3/1971 | Morane | 222/136 |
| 3,794,068 A * | 2/1974 | Milroy | 137/497 |
| 3,884,228 A | 5/1975 | Hahn | |
| 5,009,251 A | 4/1991 | Pike et al. | |
| 5,380,287 A | 1/1995 | Kikuchi et al. | |
| 5,395,340 A * | 3/1995 | Lee | 604/151 |
| 5,499,968 A * | 3/1996 | Milijasevic et al. | 604/30 |
| 5,607,418 A * | 3/1997 | Arzbaecher | 604/891.1 |
| 5,632,315 A | 5/1997 | Rose | |
| 5,840,071 A * | 11/1998 | Kriesel et al. | 604/132 |
| 6,056,716 A | 5/2000 | D'Antonio et al. | |
| 6,126,642 A * | 10/2000 | Kriesel et al. | 604/207 |
| 6,236,624 B1 | 5/2001 | Kriesel et al. | |
| 6,355,019 B1 | 3/2002 | Kriesel et al. | |
| 6,416,495 B1 | 7/2002 | Kriesel et al. | |
| 2005/0038387 A1* | 2/2005 | Kriesel et al. | 604/133 |
| 2005/0277882 A1* | 12/2005 | Kriesel | 604/131 |
| 2005/0277883 A1* | 12/2005 | Kriesel | 604/131 |

* cited by examiner

*Primary Examiner* — Laura A Bouchelle
*Assistant Examiner* — Scott Medway
(74) *Attorney, Agent, or Firm* — James E. Brunton

(57) ABSTRACT

A dispensing device for dispensing medicaments to a patient that is made up of first and second stand-alone, interconnectable assemblies. The first of these assemblies comprises a fluid reservoir assembly that houses a fluid reservoir defining component while the second assembly comprises a fluid delivery and control assembly that includes a novel flow control means that functions to control the flow of medicinal fluid from the fluid reservoir of the first assembly toward the patient via a plurality of fluid flow control passageways. Because the stand-alone fluid delivery and control assembly is initially totally separate from the fluid reservoir assembly of the apparatus, the fluid flow passageways of the fluid delivery and control assembly can be effectively sterilized using conventional gamma ray sterilization techniques without adversely affecting the medicament contained within the fluid reservoir of the apparatus.

12 Claims, 21 Drawing Sheets

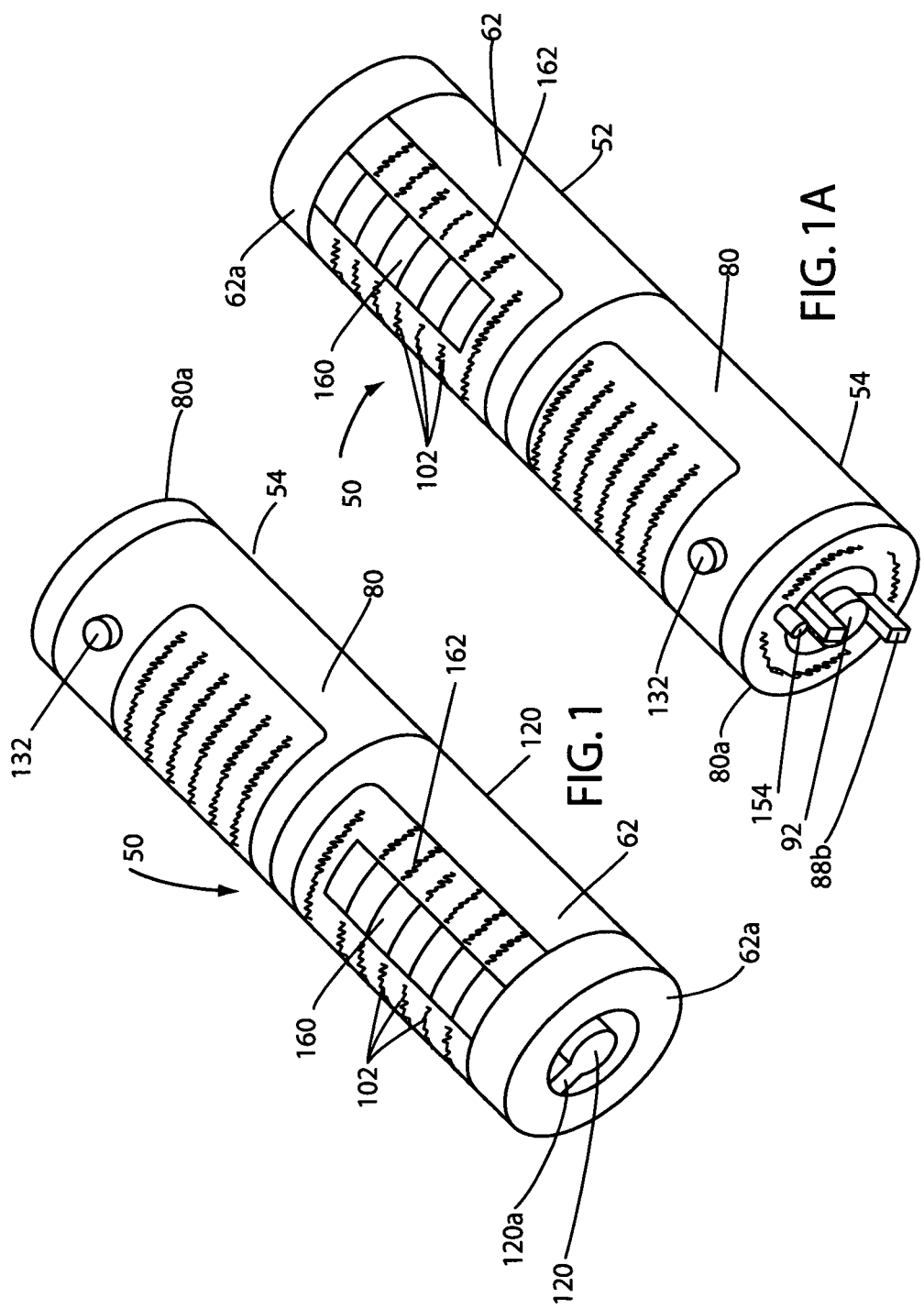

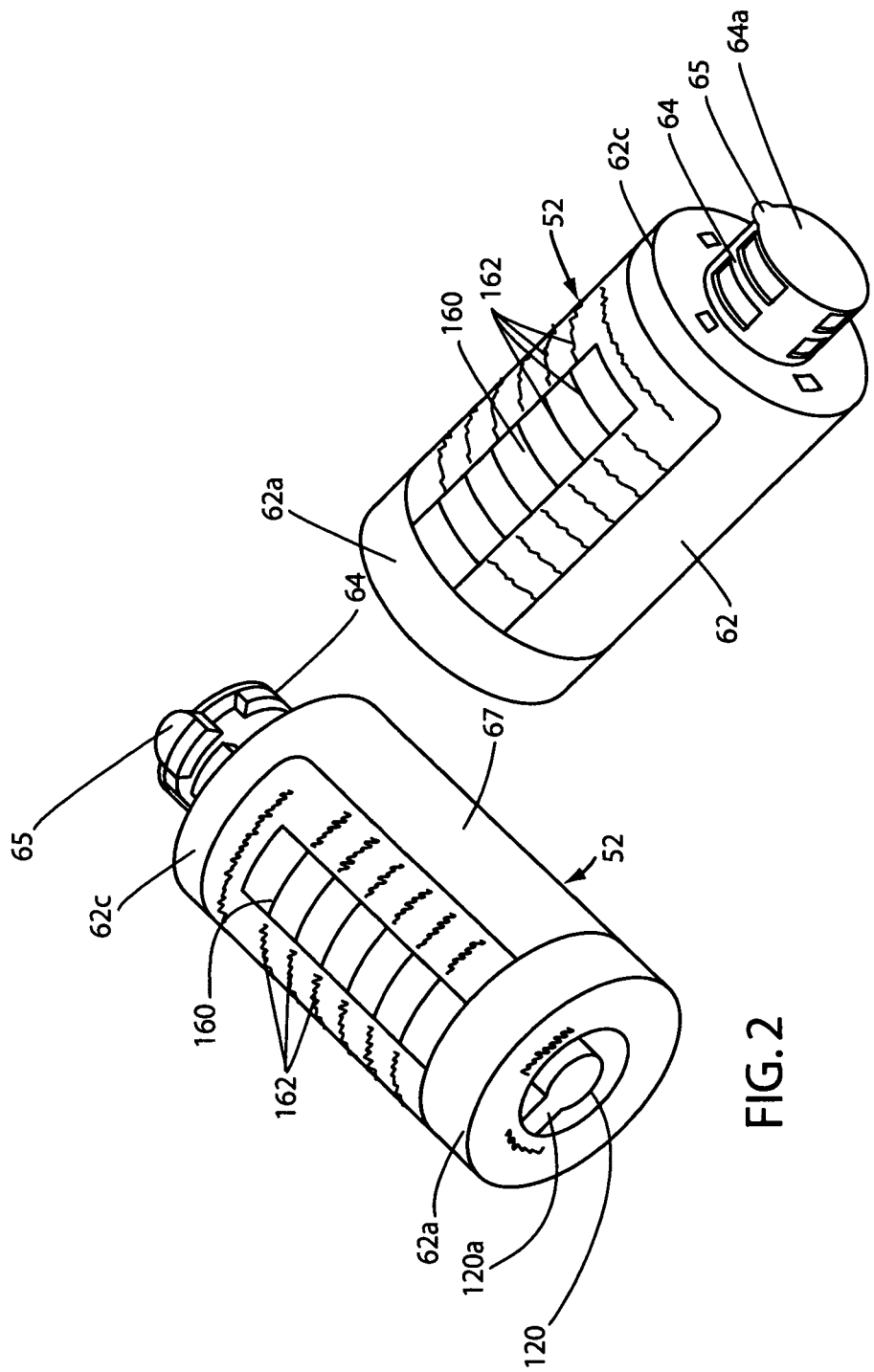

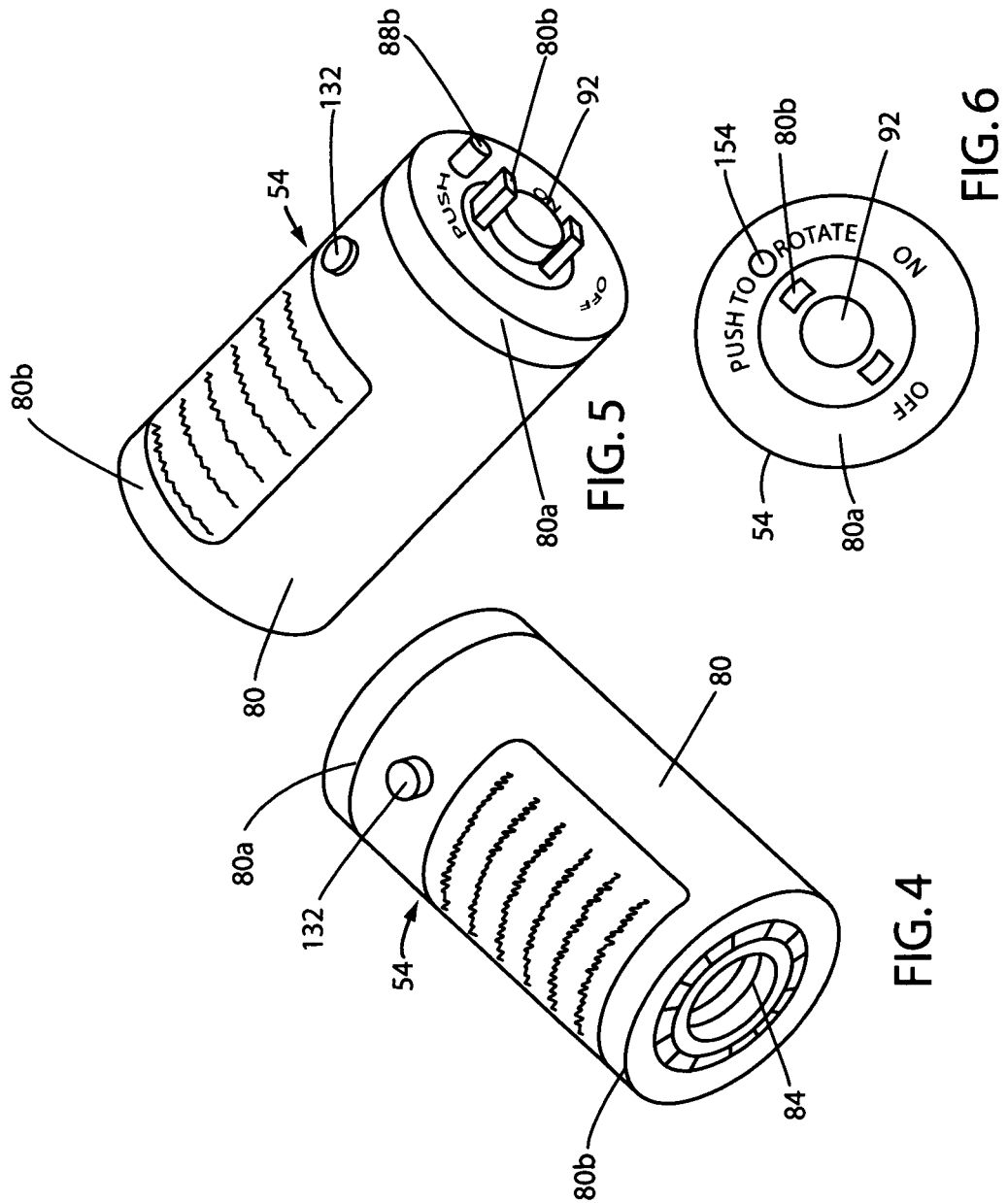

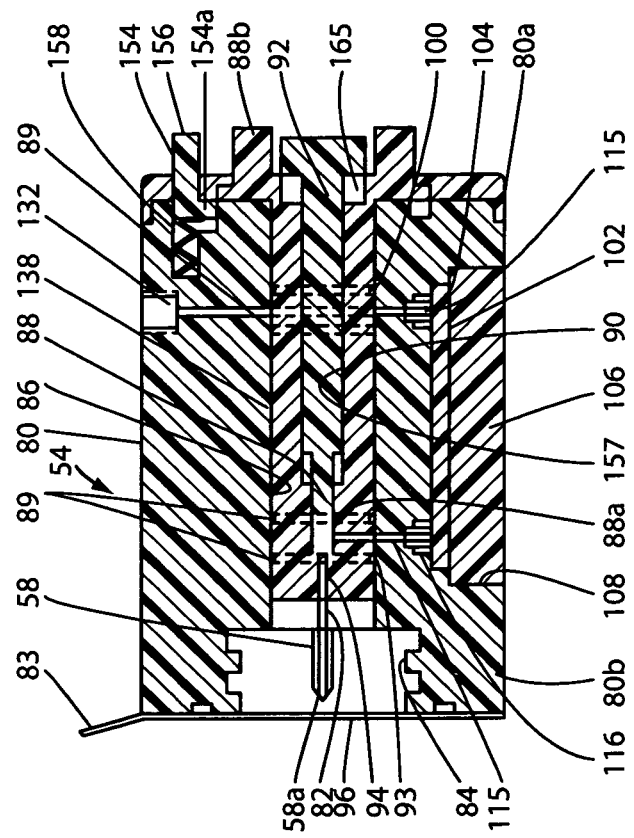
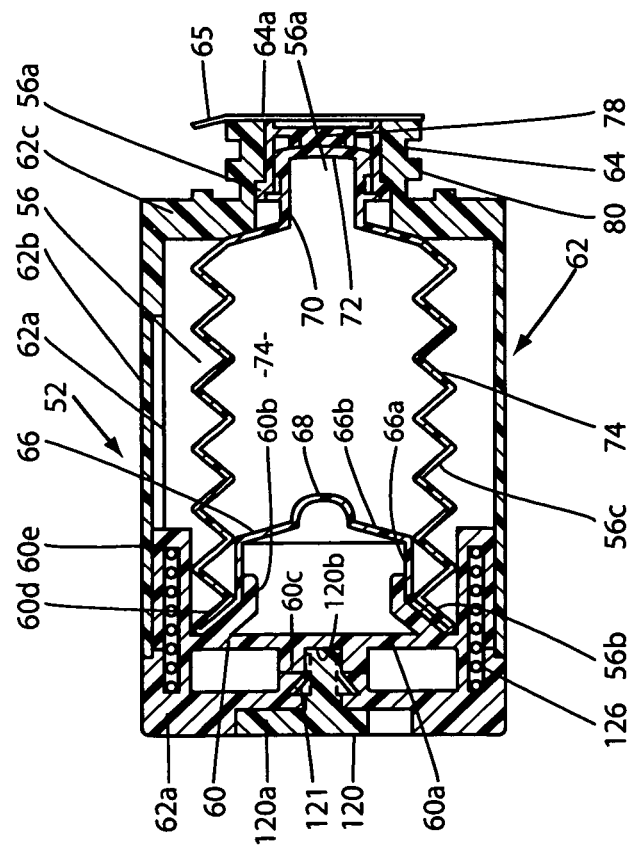
FIG. 8
FIG. 7

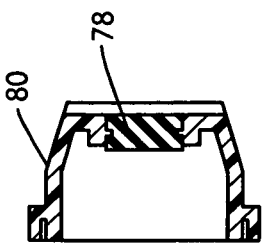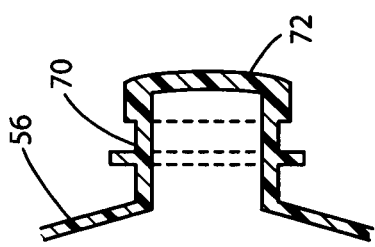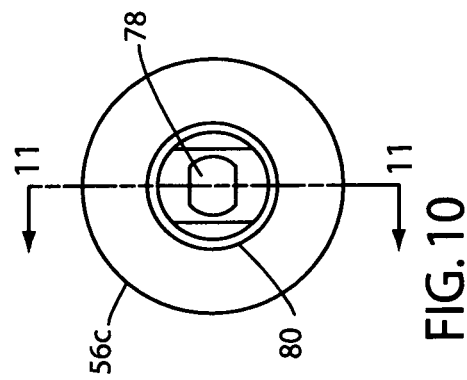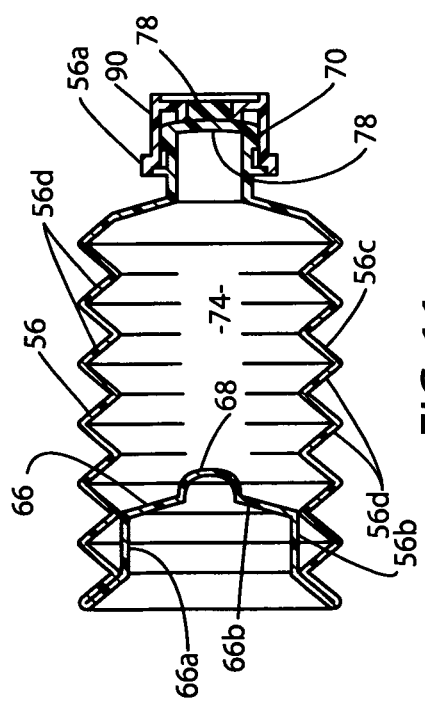

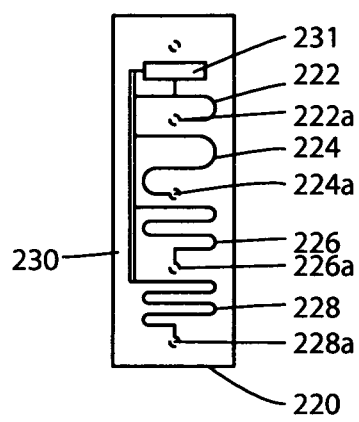
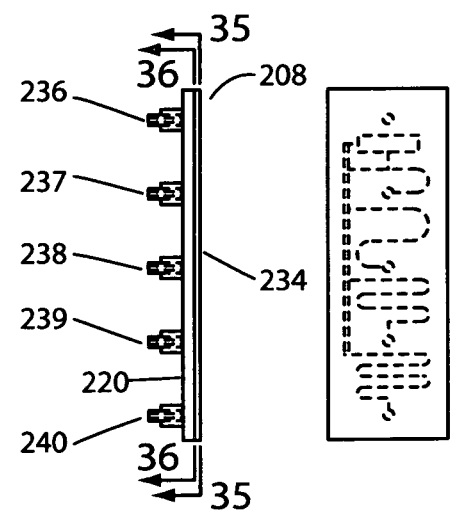
FIG. 36  FIG. 34  FIG. 35

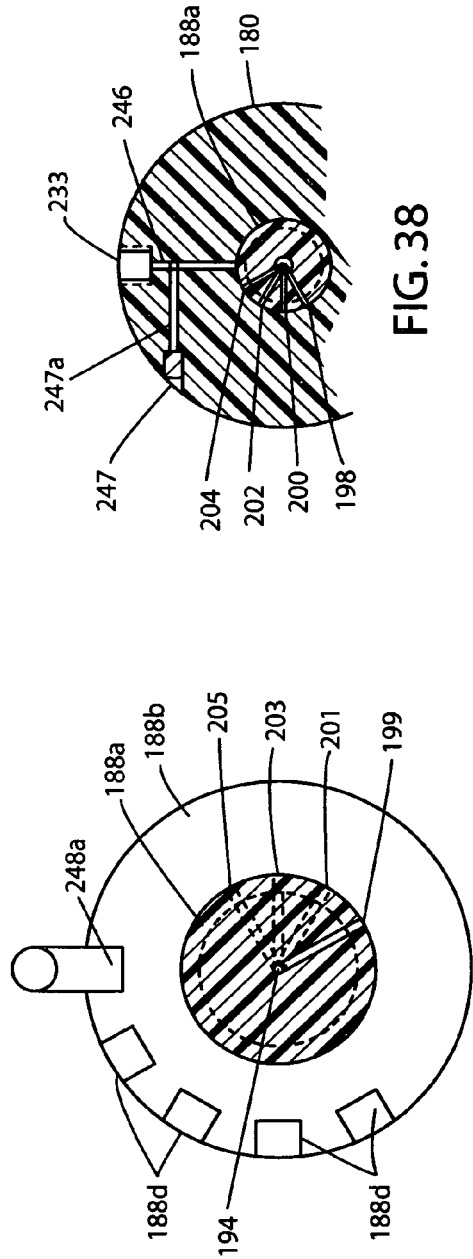
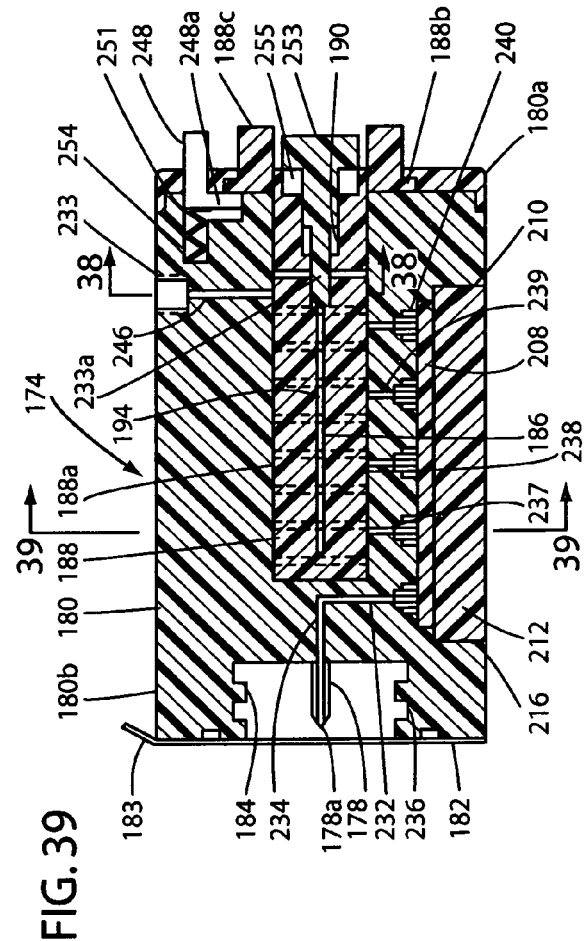
FIG. 38
FIG. 39
FIG. 37

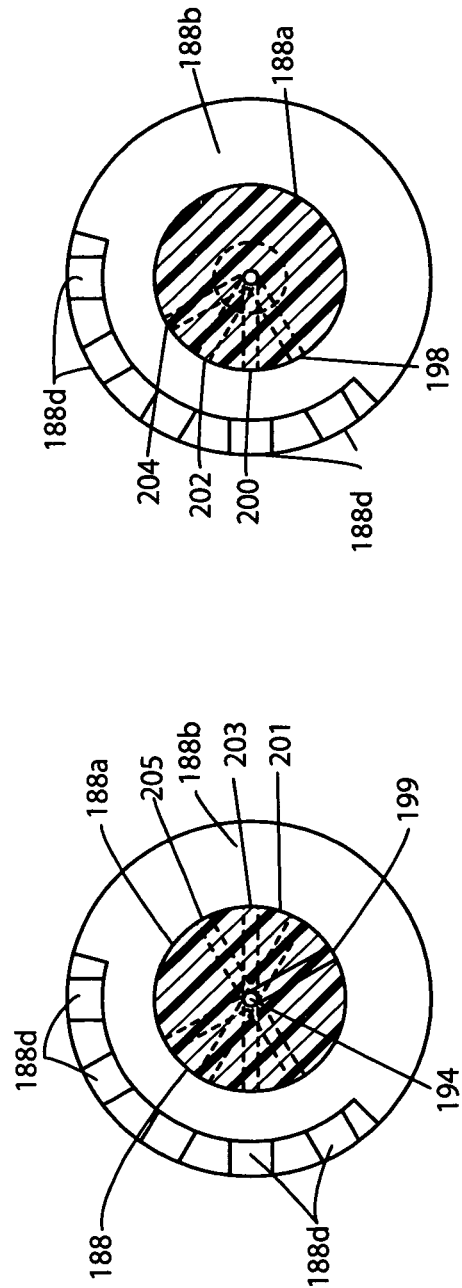
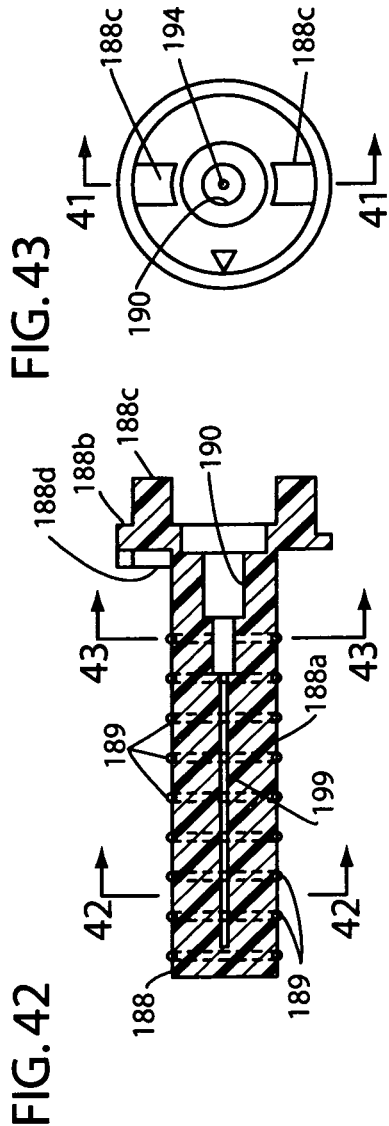
FIG. 43
FIG. 40
FIG. 41
FIG. 42

TWO PART FLUID DISPENSER

BACKGROUND OF THE INVENTION

1. Field of the Invention

The present invention relates generally to fluid dispensing devices. More particularly, the invention concerns a two part medicament dispenser for dispensing medicinal fluids to ambulatory patients that uniquely enables sterilization of the fluid flow channels without adversely affecting the medicament contained within the reservoir of the apparatus.

2. Discussion of the Prior Art

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs, bio-pharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container which is housed within the body of the device. After having been deformed, the polymeric, elastomeric member will return to its starting configuration in a highly predictable manner.

A more recent fluid dispensing apparatus invented by one of the named inventors of the present application is disclosed in U.S. Pat. No. 7,220,245. This apparatus comprises a compact fluid dispenser for use in controllably dispensing fluid medicaments, such as, antibiotics, oncolylotics, hormones, steroids, blood clotting agents, analgesics, and like medicinal agents from prefilled containers at a uniform rate. The dispenser uniquely includes a stored energy source that is provided in the form of a substantially constant-force, compressible-expandable wave spring that provides the force necessary to continuously and uniformly expel fluid from the device reservoir. The device further includes a fluid flow control assembly that precisely controls the flow of medicament solution to the patient.

SUMMARY OF THE INVENTION

By way of brief summary, one form of the dispensing device of the present invention for dispensing medicaments to a patient comprises first and second stand-alone, interconnectable assemblies. The first of these assemblies comprises a fluid reservoir assembly that houses a fluid reservoir defining component while the second assembly comprises a fluid delivery and control assembly that includes a novel flow control means that functions to control the flow of medicinal fluid from the fluid reservoir of the first assembly toward the patient via a plurality of fluid flow control passageways. A novel and highly important feature of the apparatus of the present invention resides in the fact that, because the stand-alone fluid delivery and control assembly is initially totally separate from the fluid reservoir assembly of the apparatus, the fluid flow passageways of the fluid delivery and control assembly can be effectively sterilized using conventional gamma ray sterilization techniques without adversely affecting the medicament contained within the fluid reservoir of the apparatus.

With the forgoing in mind, it is an object of the present invention to provide a novel, two-part fluid dispensing apparatus for use in controllably dispensing fluid medicaments, such as antibiotics, anesthetics, analgesics, and like medicinal agents, at a uniform rate in which the fluid flow passageways of the apparatus can be effectively sterilized using conventional gamma ray sterilization techniques without adversely affecting the medicament contained within the fluid reservoir of the apparatus.

Another object of the invention is to provide a fluid dispensing apparatus of the aforementioned character dispenser of simple construction and one that can be used in the home care environment with a minimum amount of training.

Another object of the invention is to allow infusion therapy to be initiated quickly at the point of care without the assistance of a medical professional.

Another object of the invention is to provide a novel, two part dispensing apparatus in which a stored energy source is provided in the form of a compressible, expandable or retractable member of novel construction that provides the force necessary to continuously and uniformly expel fluid from the device reservoir.

Another object of the invention is to provide a dispenser of the character described in the preceding paragraphs in which the stored energy source is provided in the form of a constant force spring that comprises a tightly coiled wound band of pre-hardened spring steel or stainless steel strip with built-in curvature so that each turn of the strip wraps tightly on its inner neighbor. When the strip is extended (deflected), the inherent stress resists the loading force; the same as a common extension spring but at a nearly constant (zero) rate.

Another object of the invention is to provide a dispenser of the class described which includes a fluid flow control assembly that precisely controls the flow of the medicament solution to the patient.

Another object of the invention is to provide a fluid dispensing apparatus that enables precise variable flow rate selection.

Another object of the invention is to provide a fluid dispensing apparatus of the character described in the preceding paragraphs that embodies an integrally formed, aseptically filled, unitary semi-rigid collapsible container that includes a fluid reservoir that contains the beneficial agents to be delivered to the patient.

Another object of the invention is to provide a fluid dispensing apparatus of the class described which is compact and lightweight, is easy for ambulatory patients to use and is extremely reliable in operation.

Another object of the invention is to provide a fluid dispensing apparatus that is easy and inexpensive to manufacture in large quantities.

BRIEF DESCRIPTION OF THE DRAWINGS

FIG. 1 is a generally perspective rear view of one form of the two-part fluid delivery system of the present invention.

FIG. 1A is a generally perspective front view of the two-part fluid delivery system illustrated in FIG. 1.

FIG. 2 is a generally perspective rear view of one form of the first stand-alone component of the invention that comprises the fluid reservoir assembly that houses a fluid reservoir defining component.

FIG. 3 is a generally perspective front view of the first stand-alone component of the invention shown in FIG. 2.

FIG. 4 is a generally perspective rear view of one form of the second stand-alone component of the invention that comprises a fluid delivery and control assembly that includes a novel flow control means that functions to control the flow of medicinal fluid from the fluid reservoir of the first stand-alone component toward the patient.

FIG. 5 is a generally perspective front view of the second stand-alone component of the invention shown in FIG. 4.

FIG. 6 is a front view of the second stand-alone component of the invention shown in FIG. 5.

FIG. 7 is a longitudinal cross-sectional view of the first stand-alone component of the invention shown in FIGS. 2 and 3 of the drawings.

FIG. 8 is a longitudinal cross-sectional view of the second stand-alone component shown in FIGS. 4, 5 and 6 of the drawings.

FIG. 10 is a front view of one form of the collapsible fluid reservoir of the first stand-alone component of the invention.

FIG. 11 is a cross-sectional view taken along lines 11-11 of FIG. 10.

FIG. 12 is an enlarged, fragmentary cross-sectional view of the forward portion of the fluid reservoir shown in FIG. 11.

FIG. 34 is a side elevational view of one form of the rate control plate assembly of the alternate second stand-alone component of the invention that includes a rate control plate and control plate cover.

FIG. 35 is a view taken along lines 35-35 of FIG. 34.

FIG. 36 is a view taken along lines 36-36 of FIG. 34.

FIG. 37 is a longitudinal cross-sectional view of the alternate form of the second stand-alone component shown in FIG. 31.

FIG. 38 is a cross-sectional view taken along lines 38-38 of FIG. 37.

FIG. 39 is a cross-sectional view taken along lines 39-39 of FIG. 37.

FIG. 40 is a front view of the rate control housing of the alternate second stand-alone component.

FIG. 41 is a cross-sectional view of the rate control housing taken along lines 41-41 of FIG. 40.

FIG. 42 is an enlarged cross-sectional view taken along lines 42-42 of FIG. 41.

FIG. 43 is an enlarged cross-sectional view taken along lines 43-43 of FIG. 41.

DESCRIPTION OF THE INVENTION

Definitions

Figure 8A:
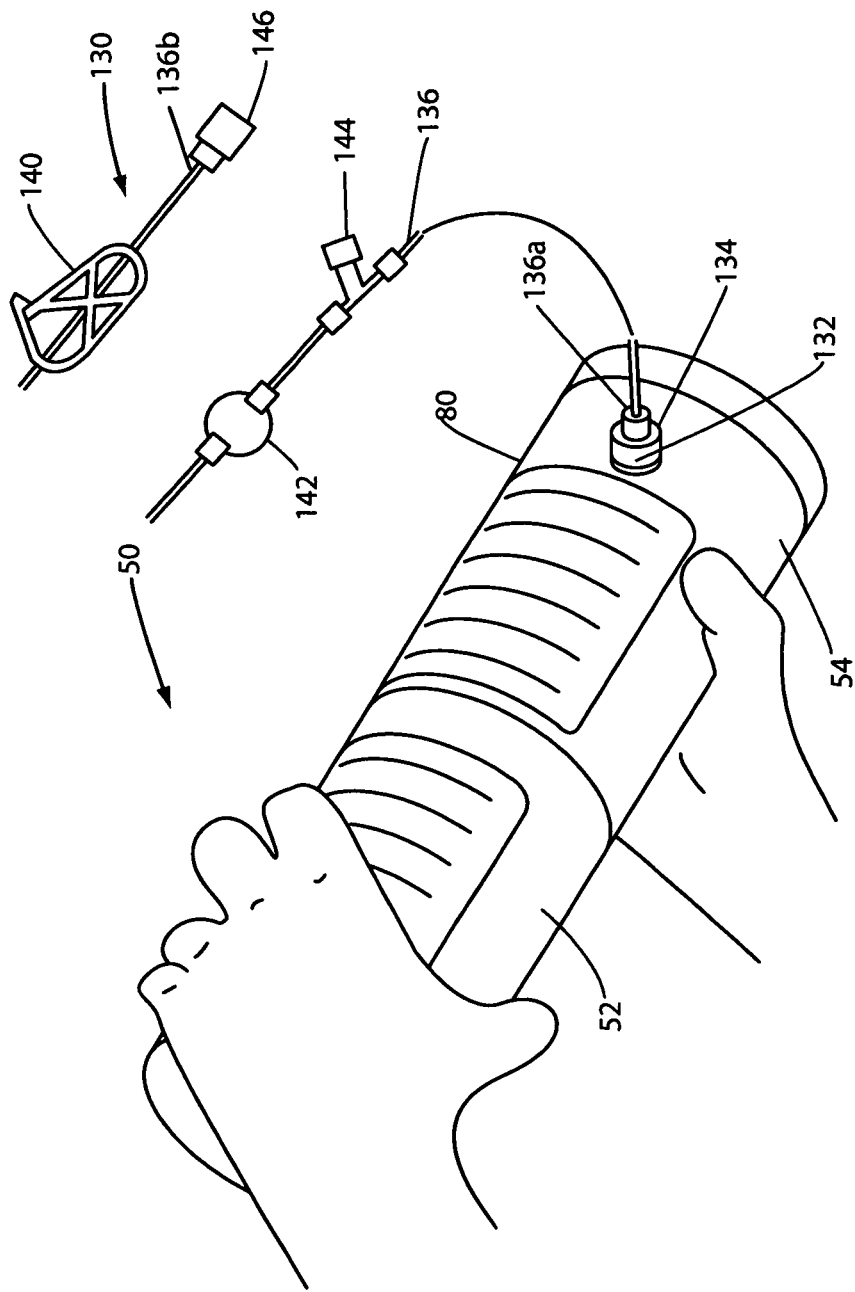
FIG. 8A is a generally perspective, diagrammatic view illustrating the assembly of the two parts of the two-part fluid delivery system of the invention.

As Used Herein the Following Terms Mean

Unitary Container
  A closed container formed from a single component.
Continuous/Uninterrupted Wall.
  A wall having no break in uniformity or continuity.
Hermetically Sealed Container A container that is designed and intended to be secure against the entry of microorganisms and to maintain the safety and quality of its contents after pressurizing.

Aseptic Processing

The term 'aseptic processing' as it is applied in the pharmaceutical industry refers to the assembly of sterilized components and product in a specialized clean environment.

Sterile Product

A sterile product is one that is free from all living organisms, whether in a vegetative or spore state.

Blow-Fill-Seal Process

The concept of aseptic blow-fill-seal (BFS) is that a container is formed, filled, and sealed as a unitary container in a continuous manner without human intervention in a sterile enclosed area inside a machine. The process is multi-stepped; pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.

Integrally Formed

An article of one-piece construction, or several parts that are rigidly secured together, and smoothly continuous in form and that any such components making up the part have been then rendered inseparable.

Frangible

An article, item or object that is capable of being ruptured or broken, but does not necessarily imply any inherent materials weakness. A material object, under load that demonstrates a mechanical strain rate deformation behavior, leading to disintegration.

Spring

A mechanical element that can be deformed by a mechanical force such that the deformation is directly proportional to the force or torque applied to it. An elastic machine component able to deflect under load in a prescribed manner and able to recover its initial shape when unloaded. The combination of force and displacement in a deflected spring is energy which may be stored when moving loads are being arrested.

Collapsible

To cause to fold, break down, or fall down or inward or as in bent-over or doubled-up so that one part lies on another.

Collapsible Container

A dispensing apparatus in which one or more walls of the container are made of a material which will deform (collapse) when pressure is applied thereto; or a dispensing apparatus having a collapsible or telescoping wall structure.

Constant Force Spring

Constant force springs are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force; the same as a common extension spring but at a nearly constant (zero) rate. The constant-force spring is well suited to long extensions with no load build-up. In use, the spring is usually mounted with the ID tightly wrapped on a drum and the free end attached to the loading force. Considerable flexibility is possible with constant-force springs because the load capacity can be multiplied by using two or more strips in tandem, or back-to-back. Constant force springs are available in a wide variety of sizes.

Referring to the drawings and particularly to FIGS. 1 through 8, one form of the two part fluid dispensing apparatus of the present invention for dispensing medicaments is there shown. The dispensing apparatus, which is generally designated in FIGS. 1, 1A and 8A by the numeral 50, comprises two stand-alone, interconnectable assemblies 52 and 54. As best seen in FIG. 7 of the drawings, assembly 52 comprises a fluid reservoir assembly that houses a fluid reservoir defining component 56 having an outlet 56a. As illustrated in FIG. 8 of the drawings, assembly 54 comprises a fluid delivery and control assembly that includes a penetrating member 58 and a novel fluid flow control means that functions to control the flow of medicinal fluid toward the patient.

Figure 16:
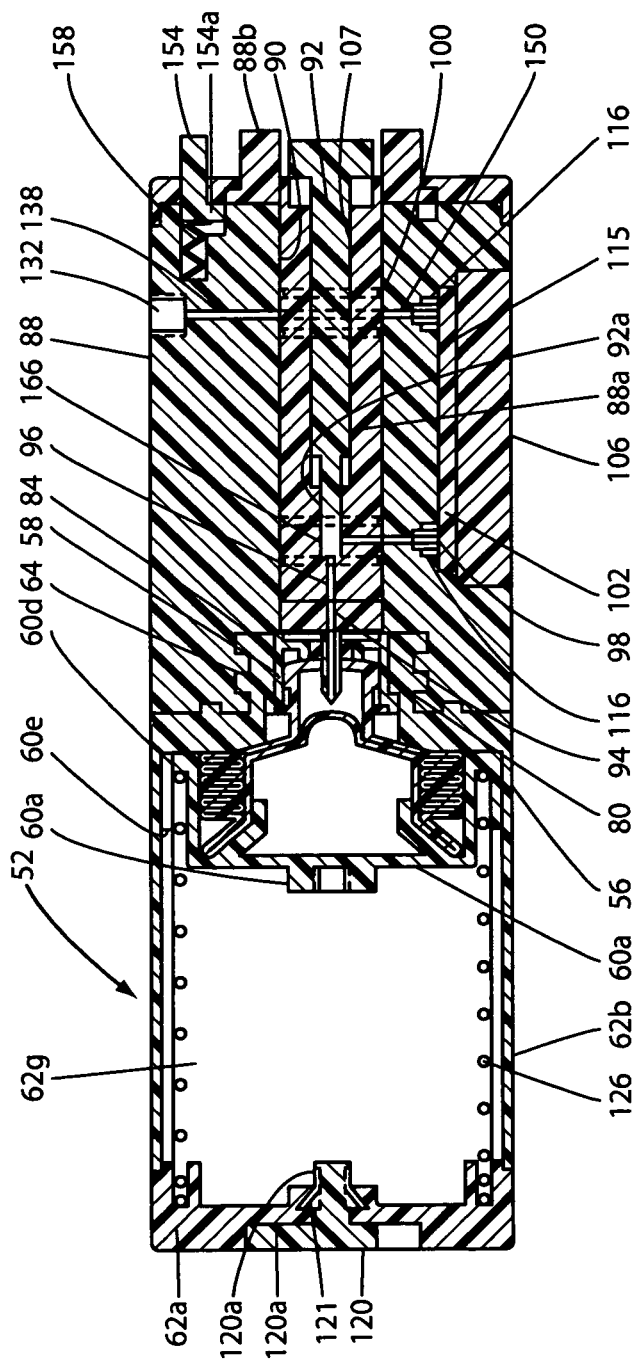
FIG. 16 is a longitudinal cross-sectional view of the fluid dispensing apparatus of the invention shown in FIG. 1, wherein the first and second stand-alone components of the invention have been operably interconnected.

Considering first the unitary fluid reservoir assembly 52, in addition to the reservoir defining component 56, this assembly includes a carriage 60 and a stored energy means that is operably associated with the carriage for moving the carriage between a first retracted position shown in FIG. 7 and a second advanced position shown in FIG. 16. As best seen by referring to FIG. 7, carriage 60 includes a base 60a, a reservoir receiving flange 60b, a carriage locking member receiving protuberance 60c and a stored energy means receiving skirt 60d which receives the novel stored energy means of the invention. Carriage 60 is releasably locked in its first position by a novel carriage locking means, the character of which will be described in the paragraphs which follow.

The reservoir defining component 56, the carriage 60 and a stored energy means are all housed within a generally cylindrically shaped housing 62 that includes a base 62a, an outer wall 62b and a front wall 62c. Connected to front wall 62c is an externally threaded connector neck 64. Connector neck 64 is closed by a first cover shown here as a first sterile barrier 64a that is removably connected to the connector neck in the manner shown in FIG. 7 of the drawings. Sterile barrier 64a, which includes a pull tab 65, here comprises a thin membrane constructed from any suitable polymer.

As best seen in FIG. 11, reservoir defining component 56 here comprises an integrally formed, hermetically sealed container that includes a front portion 56a, a rear portion 56b and a collapsible accordion-like, continuous, uninterrupted side wall 56c that interconnects the front and rear portion of the container. As illustrated in the drawings, the accordion like side wall 56c comprises a multiplicity of adjacent generally "V" shaped interconnected folds, 56d. Rear portion 56b of the container includes an inwardly extending ullage segment 66 having a side wall 66a and an end wall 66b. As illustrated in FIGS. 7 and 11, end wall 66b includes a generally hemispherical shaped protuberance 68. Front portion 56a of the container includes an integrally formed neck 70 having a closure wall 72. Front portion 56a, rear portion 56b and side wall 56c cooperate to define the fluid reservoir 74 of the fluid reservoir assembly 52.

Reservoir defining component 56 is constructed in accordance with aseptic blow-fill seal manufacturing techniques the character of which is well understood by those skilled in the art. Basically, this technique involves the continuous plastic extrusion through an extruder head of a length of parison in the form of a hollow tube between and through two co-acting first or main mold halves. The technique further includes the step of cutting off the parison below the extruder head and above the main mold halves to create an opening which allows a blowing and filling nozzle assembly to be moved downwardly into the opening in the parison for molding and then filling the molded container in a sterile fashion. Following the molding, filling and sealing of the container, it is sterilized at high temperature in a manner well understood by those skilled in the art. Unlike chemical or gamma ray sterilization, this temperature sterilization step has no adverse effect on the medicament contained within the container reservoir.

Containers for use in dispensing beneficial agents in specific dosages, such as the unidose reservoir assembly of the present invention present unique requirements. More particularly, it is important that as much of the beneficial agents contained within the reservoir assembly be dispensed from a container to avoid improper dosage, waste and undue expense. Accordingly the previously identified ullage segment functions to fill the interior space of the collapsible container when it is collapsed in the manner shown in FIG. 16 of the drawings.

In a manner presently to be described, fluid medicament reservoir 74 of the fluid reservoir assembly 52 is accessible via a penetrating member 58 which forms the inlet to the fluid delivery and control assembly 54. More particularly, penetrating member 58 is adapted to pierce closure wall 72 as well as a pierceable membrane 78 (FIGS. 7, 11 and 12) which is secured in position over closure wall 72 by means of a closure cap 80 which is affixed to the neck portion 70 of reservoir defining assembly 56 (FIG. 11). As previously described, the reservoir defining assembly 56 is formed using the earlier described aseptic blow fill technique and the reservoir portion of the container is sealed by the thin closure wall 72. Prior to heat sterilization of the container, the pierceable membrane 78 is positioned over the closure wall and the closure cap 80 is positioned over the pierceable membrane and is secured to the neck portion 70 by any suitable means such as adhesive bonding, sonic welding or heat welding.

Considering now the second assembly 54 of the fluid dispensing apparatus, which is illustrated in FIGS. 4, 5, 6 and 8, this assembly comprises a generally cylindrically shaped housing 80 having a forward portion 80a and a rearward portion 80b. Rearward portion 80b which is covered by a cover, here shown as a second sterile barrier 82 having a pull tab 83, includes an internally threaded cavity 84. Second sterile barrier 82, which is removably connected as by bonding to rearward portion 80b in the manner shown in FIG. 8 of the drawings, here comprises a thin membrane constructed from any suitable polymer.

As illustrated in FIG. 8 of the drawings, housing 80 includes a longitudinally extending bore 86 that rotatably receives the rate control housing 88 of the second assembly 54. Rate control housing 88, which forms a part of the flow control means of the invention, includes an elongated body portion 88a and a forwardly extending finger engaging portion 88b. A plurality of longitudinally spaced apart O-rings 89, which circumscribe body portion 88a, function to prevent fluid leakage between housing 80 and the body portion 88a of the rate control housing. Elongated body portion 88a is also provided with a longitudinally extending bore 90 that slidably receives a disabling shaft 92, the construction and operation of which will presently be described.

Figure 17:
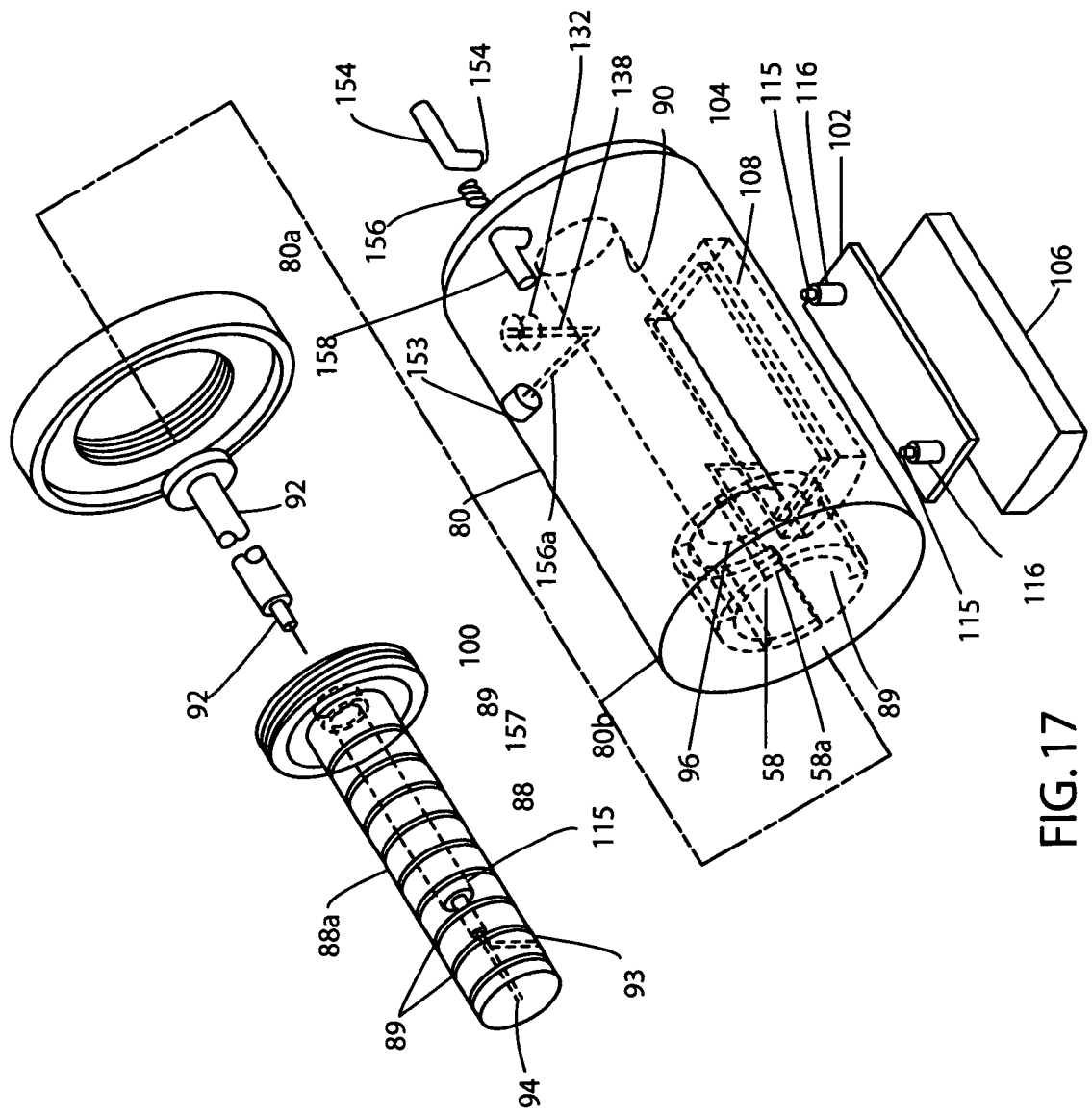
FIG. 17 is a generally perspective, exploded view of the second stand-alone component shown in FIGS. 4, 5 and 6.
Figure 22:
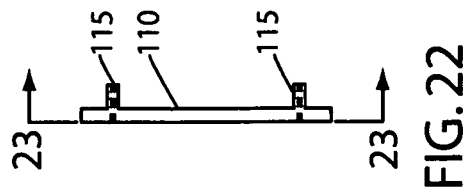
FIG. 22 is a side elevational view of the rate control plate of the rate control plate assembly shown in FIG. 18.

As illustrated in FIGS. 8 and 17, body portion 88a is also provided with a longitudinally extending fluid passageway 94 that communicates with the flow passageway 58a of the previously identified piercing member 58 via a passageway 96 provided in housing 80. For a purpose presently to be described, body portion 88a is also provided with a pair of longitudinally spaced fluid flow passageways 98 and 100.

Fluid flow passageway 98 comprises an inlet passageway that communicates with a rate control assembly 102 that is mounted within a cavity 104 provided in a housing 80. Rate control assembly 102, which also forms a part of the flow control means of the invention, is maintained within cavity 104 by a rate control cover 106, which also forms a part of the flow control means of the invention. As best seen in FIG. 8 of the drawings, rate control cover 106 is disposed within a cavity 108 formed in housing 80.

As previously mentioned, since assembly 54 comprises a stand alone, unitary assembly containing no medicinal fluids, it can be sterilized in the preferred manner by irradiating it with gamma-rays.

Figure 23:
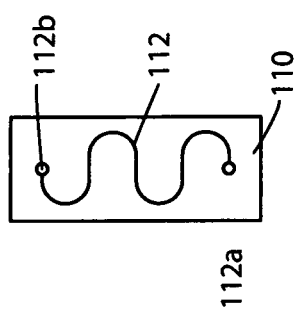
FIG. 23 is a view taken along lines 23-23 of FIG. 22.
Figure 20:
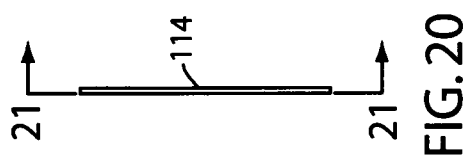
FIG. 20 is a side elevational view of one form of the rate control plate cover of the second stand-alone component.
Figure 21:
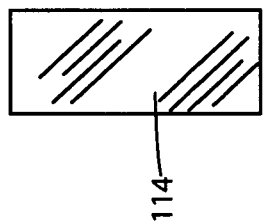
FIG. 21 is a view taken along lines 21-21 of FIG. 20.
Figure 18:
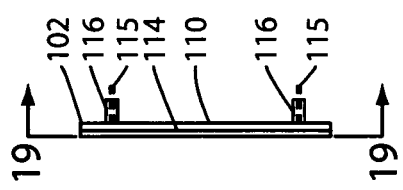
FIG. 18 is a side elevational view of one form of the rate control plate assembly of the second stand-alone component that includes a rate control plate and the rate control plate cover.
Figure 19:
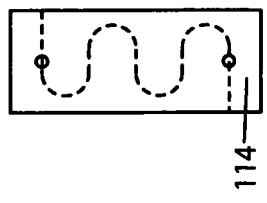
FIG. 19 is a view taken along lines 19-19 of FIG. 18.
Figure 29:
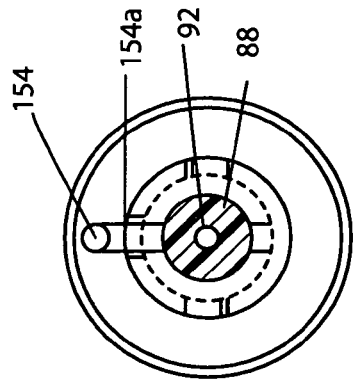
FIG. 29 is a rear view of the second stand-alone component of the invention.

As best seen in FIGS. 18 through 22, rate control assembly 102 comprises a rate control plate 110, which as shown in FIG. 23 is provided with a serpentine micro-channel 112 having an inlet 112A and an outlet 112b which communicates with passageway 100 that comprises an outlet passageway. The length, width and depth of the micro-channel determine the rate at which the fluid will flow toward outlet 112b. A thin cover 114 covers the channel in the manner shown in FIG. 18. When assemblies 52 and 54 are interconnected in the manner shown in FIG. 16, inlet 112A is in communication with penetrating member 58 via an outlet tube 115 that is received within and positioned by an upstanding collar 116 provided on rate control plate 110, via passageway 98, via passageway 94 and via passageway 96 (FIG. 8). Because the second assembly has been sterilized in the manner previously described, these passageways are completely sterile at the time assembly 54 is connected to assembly 52.

In using the apparatus of the invention, the first step is to remove the sterile covers 64a and 82 from assemblies 52 and 54. This done, the assemblies can be irreversibly interconnected in the manner illustrated in FIG. 8A by inserting the externally threaded neck 64 of assembly 52 into internally threaded cavity 84 of assembly 54 and rotating assembly 52 relative to assembly 54. As the assemblies mate, penetrating member 58 will penetrate elastomeric member 78 and closure wall 72 of the container.

Figure 9:
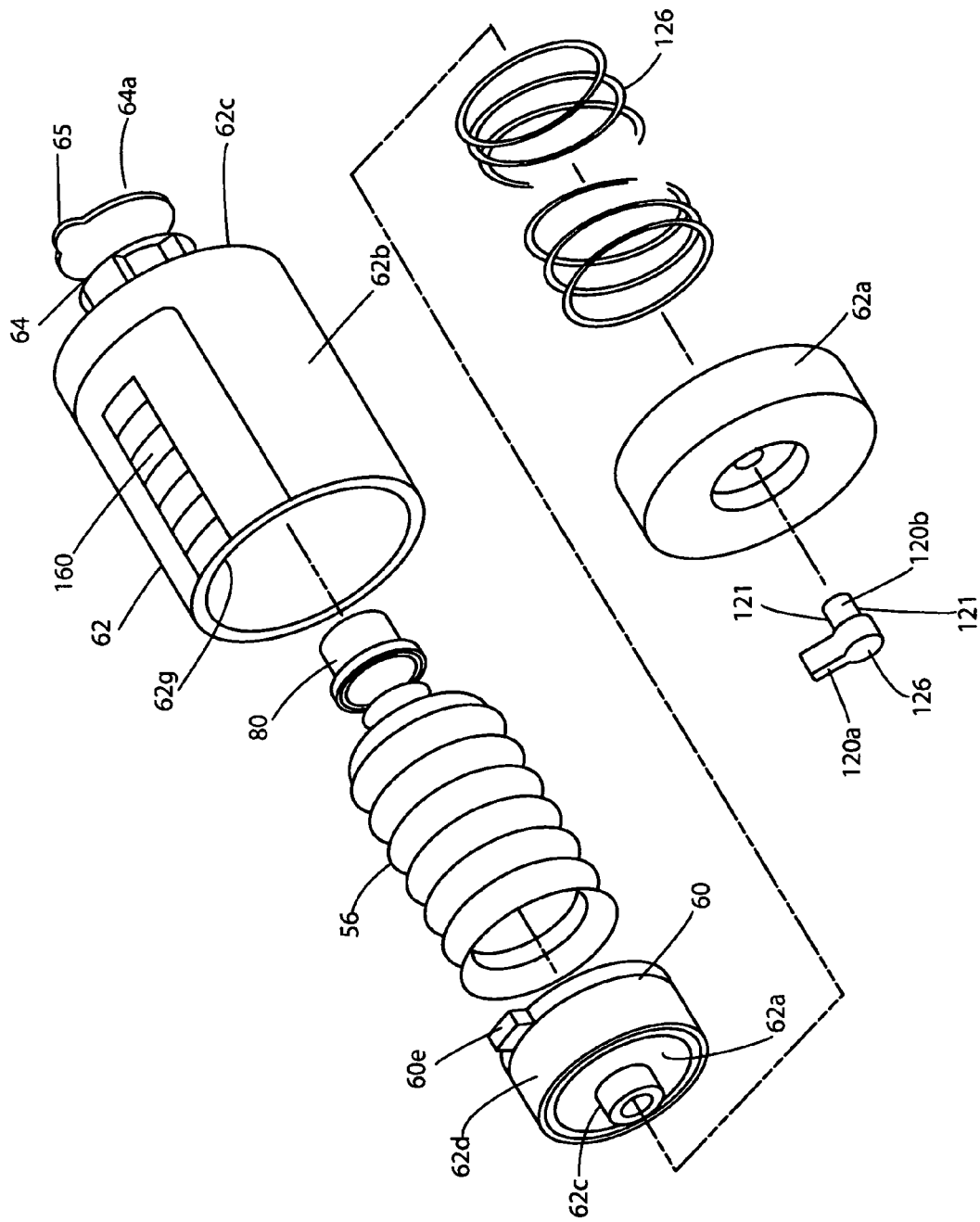
FIG. 9 is a generally perspective, exploded view of the first stand-alone component shown in FIGS. 2 and 3.
Figure 13:
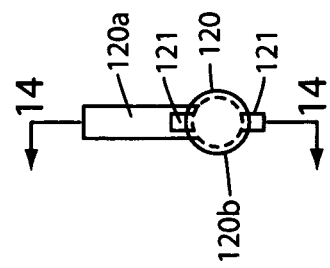
FIG. 13 is a front view of one form of the carriage locking member of the first stand-alone component of the invention.
Figure 14:
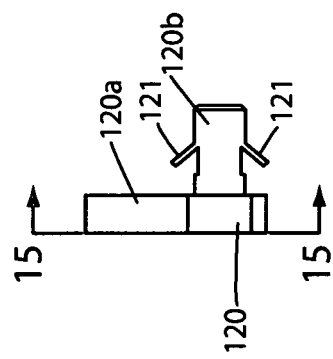
FIG. 14 is a cross-sectional view taken along lines 14-14 of FIG. 13.
Figure 15:
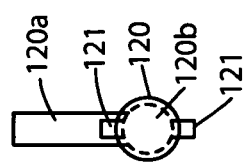
FIG. 15 is a view taken along lines 15-15 of FIG. 14.

With communication between the fluid reservoir 74 and the internal fluid passageway 58a of the penetrating member 58 having thusly been established, the fluid contained within the fluid reservoir can be expelled from the reservoir 74 by rotating the carriage release member 120 which comprises a part of the previously identified carriage locking means. This is accomplished by grasping the finger engaging arm 120A of the release member (FIG. 14) and rotating the member in the manner indicated in FIG. 2 until the threaded shank 120b of the knob threadably disengages from the locking member receiving protuberance 60c. Release member 120 is held in position within housing base 62a by means of circumferentially spaced locking tabs 121 provided on shank 120b. Once the carriage release member is free from the locking member receiving protuberance, the stored energy means, here shown as a coil spring 126 that is movable from the first compressed position shown in FIG. 7 to a second extended position shown in FIG. 16, will urge the carriage forwardly in the manner illustrated in FIG. 16 of the drawings. As the carriage moves forwardly, the circumferentially spaced guide tabs 60e formed on the carriage (FIG. 9) will slide within and be guided by guide channel 62g formed in housing 62 (FIG. 7). As the accordion side walls collapse, the fluid will be forced outwardly of the reservoir into internal passageway 58a of the penetrating member. In the manner previously described, the fluid will then flow toward the fluid flow control means of the invention, which functions to control the flow of fluid from the fluid reservoir of the fluid delivery portion of the device toward the patient.

To enable the fluid to flow from the reservoir 74 to the patient via the administration set 130 (FIG. 8A), the fluid control locking means must be operated in the manner presently to be described.

As shown in FIG. 8A of the drawings, the administration set 130 is sealably interconnected with an outlet port 132 formed in housing 80. More particularly, the administration set 130 is connected to housing 80 by means of a connector 134 so that the proximal end 136a of the administration line 136 is in communication with an outlet fluid passageway 138 formed in housing 80 (see FIG. 8). Disposed between the proximal end 136a and the distal end 136b of the administration line are a conventional clamp 140, a conventional gas vent and filter 142, and a generally Y-shaped injector site, generally designated by the numeral 144. A luer connector 146 of conventional construction is provided at the distal end 136b of the administration line.

To permit fluid flow from the outlet 112b of the rate control micro-channel 112 toward passageway 138, the rate control housing 88 must be rotated to a position wherein flow passageway 100 aligns with a flow passageway 150 formed in housing 80 (FIG. 8) and also with outlet passageway 138. Since passageway 150 is in communication with outlet 112b of the rate control channel, fluid can flow through the micro-channel at a controlled, fixed rate depending upon the configuration of the channel, into passageway 150, then into passageway 100, then through the rate control housing and finally into passageway 138. From passageway 138 the fluid will flow into the inlet of the administration set for delivery to the patient at a predetermined fixed rate. During the fluid delivery step any gases contained within the device reservoir and the various fluid passageways are vented to atmosphere via vent port 153 and passageway 153a (FIG. 17).

Figure 26:
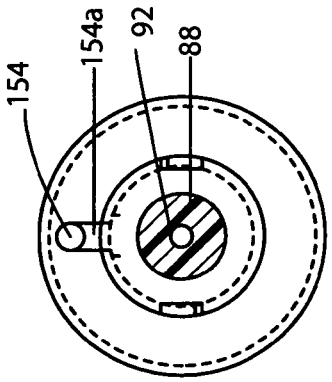
FIG. 26 is a rear view of the second stand-alone component of the invention.
Figure 27:
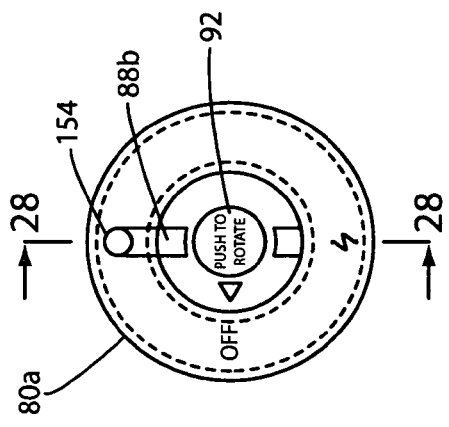
FIG. 27 is a front view of the second stand-alone component of the invention is illustrating the operation of the disabling mechanism.
Figure 24:
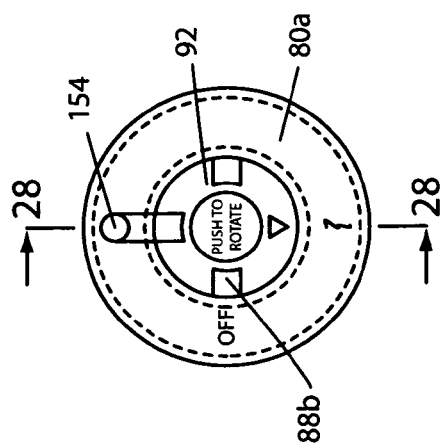
FIG. 24 is a front view of the second stand-alone component of the invention is illustrating the operation of the locking plunger of the device to accomplish the fluid dispensing step.
Figure 28:
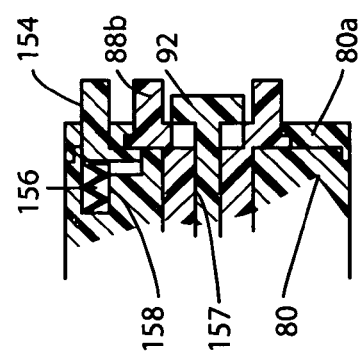
FIG. 28 is a fragmentary cross-sectional view taken along lines 28-28 of FIG. 27.
Figure 25:
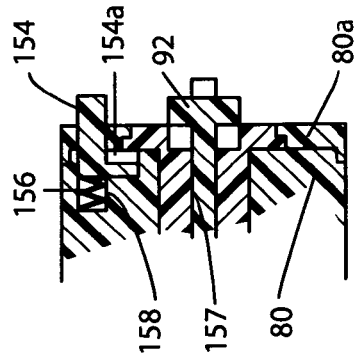
FIG. 25 is a fragmentary cross-sectional view taken along lines 25-25 of FIG. 24.

As previously mentioned, rotation of the rate control housing 88 cannot be accomplished until the rate control locking means is operated by the caregiver. In the present form of the invention this rate control locking means comprises a plunger 154 that includes a locking finger 154a (FIG. 17) that prevents rotation of the rate control housing, unless and until the plunger is moved inwardly of the housing against the urging of a biasing means shown here as coil spring 156 that is housed within a chamber 158 formed in housing 80. Once the plunger is appropriately urged inwardly, rate control housing 88 can be rotated into the correct fluid flow position by grasping rotation fingers 88b and imparting a rotational force to the rotating fingers (see also FIGS. 24, 25 and 26).

Referring to FIGS. 2 and 3, it is to be noted that a reservoir viewing window 160 is provided in housing 62 so that the remaining amount of fluid contained within reservoir 74 can be viewed. Additionally, fluid level indicating indicia 162 are provided on housing 62, proximate window 160 so that the fluid remaining within the reservoir can be accurately monitored by the caregiver.

Fluid flow from the reservoir 74 toward the rate control assembly via passageway 98 can be prevented through operation of the disabling means of the invention. This important disabling means, which is illustrated in FIGS. 8 and 27 through 29, comprises the previously identified disabling shaft 92. As indicated in the drawings, when the disabling shaft 92 is pushed inwardly from the position shown in FIG. 8 into an inward position, wherein it resides within a cavity 157 provided in housing 88, the forward portion 92a of the disabling shaft will move into a cavity 165 formed in rate control housing 88, thereby blocking fluid flow from the internal passageway 58a of the penetrating member into passageway 98. By stopping fluid flow in this manner, the apparatus is substantially safely disabled until the disabling shaft 92 is once again returned to the starting position shown in FIG. 8 of the drawings.

Figures 30, 31:
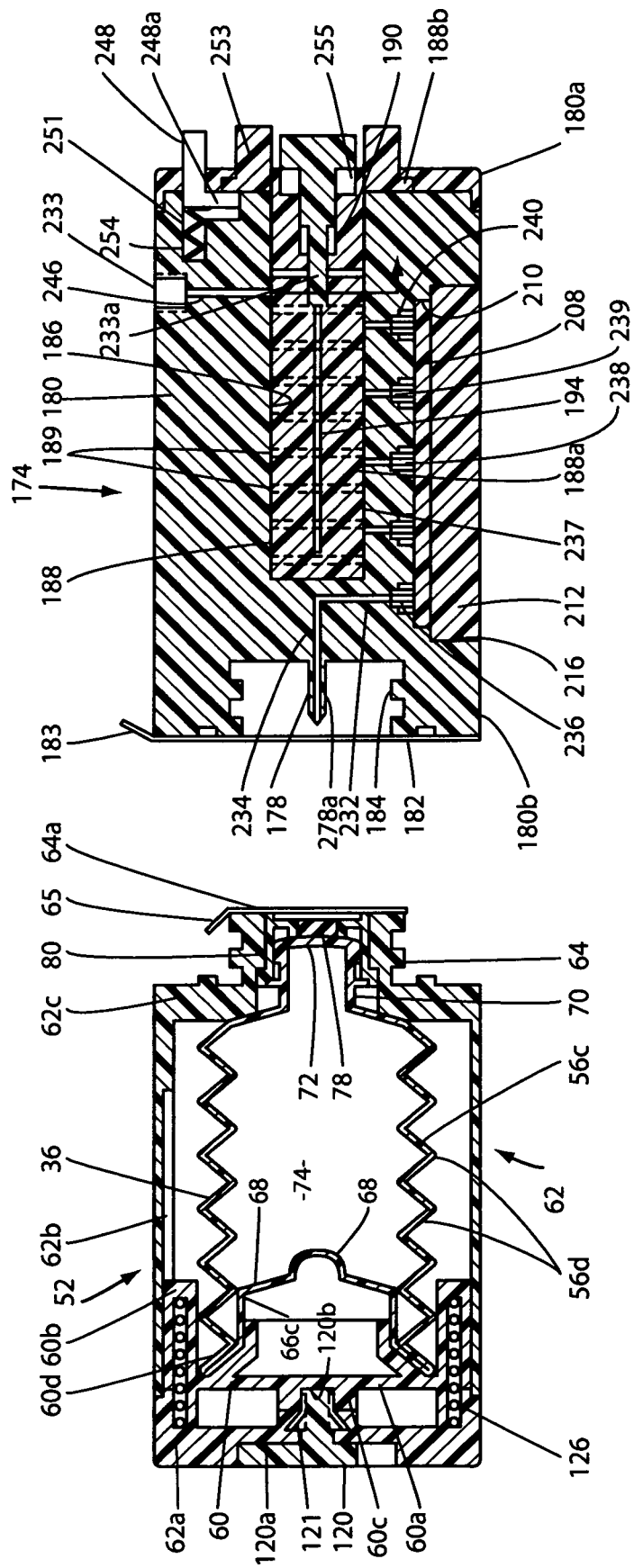
FIG. 30 is a longitudinal cross-sectional view of an alternate form of the first stand-alone component of the invention.
FIG. 31 is a longitudinal cross-sectional view of an alternate form of the second stand alone component.
Figure 32:
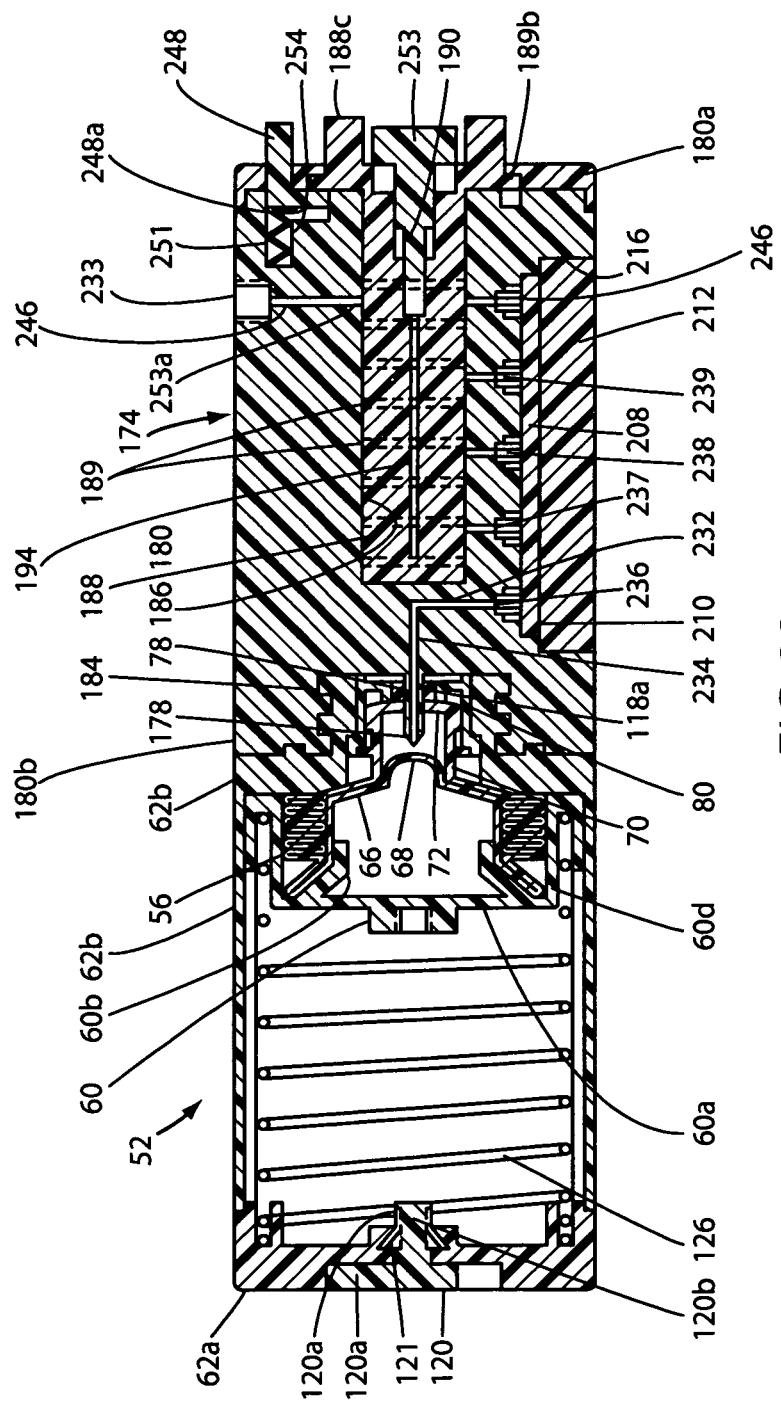
FIG. 32 is a longitudinal cross-sectional view of the fluid dispensing apparatus of the invention shown in FIG. 1 wherein the first and second stand-alone components of the invention have been operably interconnected.

Referring now to FIGS. 30, 31 and 32, an alternate form of the two part fluid dispensing apparatus of the present invention for dispensing medicaments is there shown. This alternate form of dispensing apparatus, which is generally designated in FIG. 32 by the numeral 174, is similar in many respects to the embodiment of the invention illustrated in FIGS. 1 through 29 and like numerals are used in FIGS. 30, 31 and 32 to identify like components. As before, the dispensing apparatus here comprises two stand-alone, interconnectable assemblies 52 and 174. As indicated in FIG. 30, first assembly 52 is substantially identical in construction and operation to the previously described first assembly and comprises a fluid reservoir assembly that houses a fluid reservoir defining component 56. Assembly 174 is also somewhat similar to the previously described assembly 54 and comprises a fluid delivery and control assembly that includes a penetrating member 178 and a novel fluid flow control means that functions to control the flow of medicinal fluid toward the patient. The primary difference between second assembly 174 and the previously described assembly 54 resides in the provision of a differently constructed rate control assembly that permits the delivery of fluid to the patient at a plurality of selected rates of flow As in the earlier described embodiment of the invention, reservoir defining component 56 is constructed in accordance with aseptic blow-fill seal manufacturing techniques. Following molding, filling in the sealing, the reservoir defining component is sterilized at a relatively high temperature.

In a manner presently to be described, fluid medicament reservoir 74 of the fluid reservoir assembly 52 is accessible via the previously identified penetrating member 178 which forms to inlet to the fluid delivery and control assembly 174. More particularly, penetrating member 178 is adapted to pierce closure wall 72 as well as a pierceable membrane 78 (FIG. 32) which is positioned over closure wall 72 of by means of a closure cap 80 that is affixed to the neck portion 70 of reservoir defining assembly 56 (FIG. 11).

Figure 33:
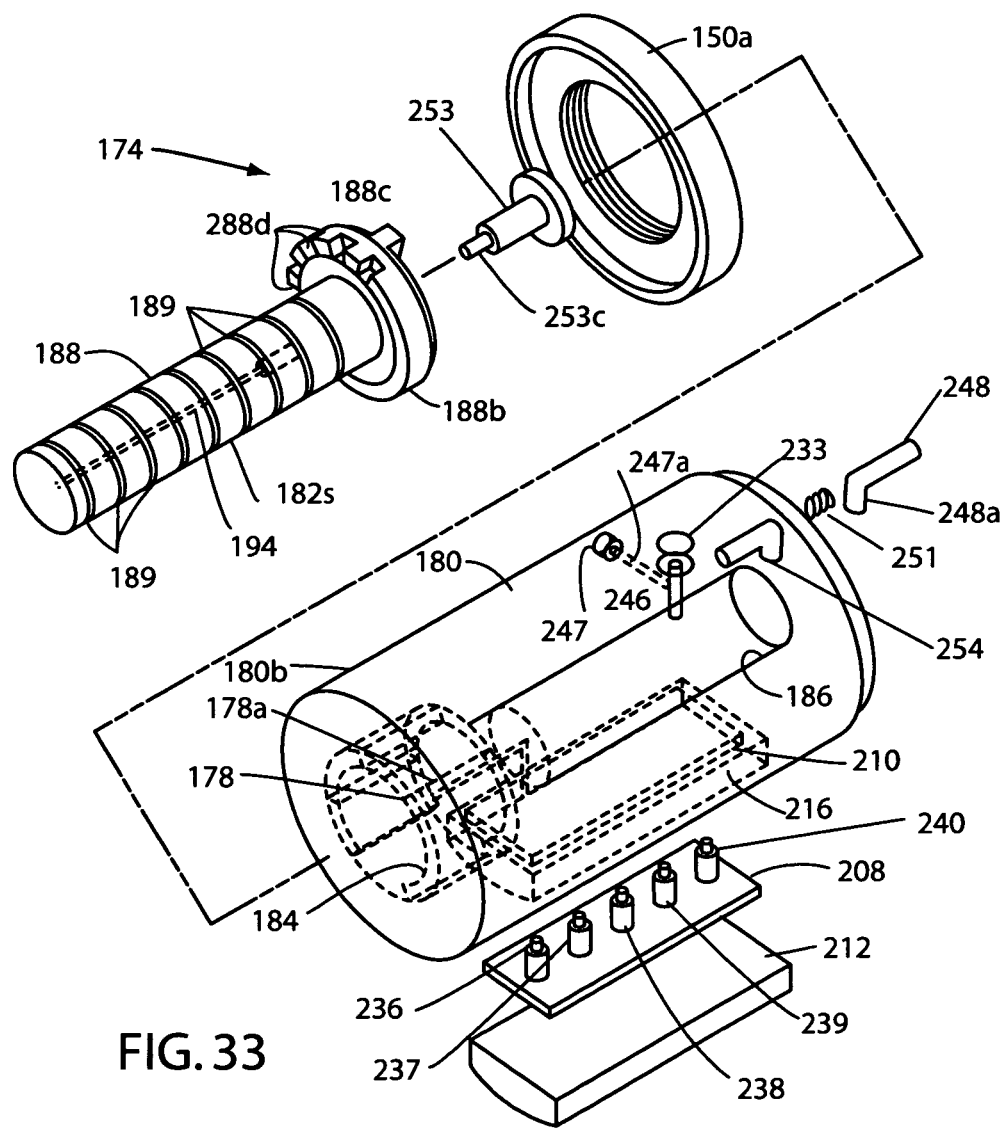
FIG. 33 is a generally perspective, exploded view of the alternate second stand alone component shown in FIGS. 4, 5 and 6.
Figure 46:
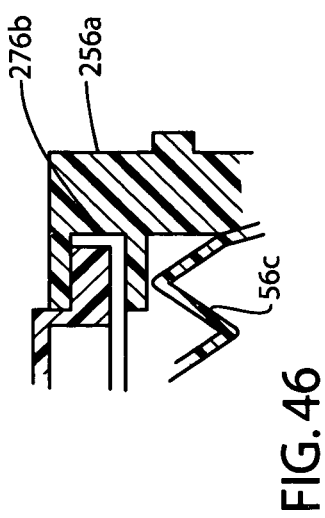
FIG. 46 is an enlarged fragmentary cross-sectional view of the portion identified as 46 in FIG. 44.

Considering now the second assembly 174 of this latest form of the fluid dispensing apparatus which is illustrated in FIGS. 31, 33 and 37, this assembly comprises a generally cylindrically shaped housing 180 having a forward portion 180a and a rearward portion 180b. Rearward portion 180b, which is sealed by a second hermetically affixed sterile barrier 182 having a pull tab 183, includes an internally threaded cavity 184. Second sterile barrier 182, which is removably connected to rearward portion 180b in the manner shown in FIGS. 31 and 37 of the drawings, here comprises a thin membrane constructed from any suitable polymer.

As illustrated in FIGS. 31, 33 and 37 of the drawings, housing 180 includes a longitudinally extending bore 186 that rotatably receives the rate control housing 188 of the second assembly 174. Rate control housing 188, which forms a part of the flow control means of this latest embodiment of the invention, includes an elongated body portion 188a, forward flange 188b and a forwardly extending finger engaging portion 188c that is connected to and extends forwardly of flange 188b. For a purpose presently to be described, a plurality of circumferentially spaced apart channels, or cavities, 188d are formed on the rear face of flange 188b. Additionally, a plurality of longitudinally spaced apart O-rings 189, which circumscribe body portion 188a, function to prevent fluid leakage between housing 180 and the body portion 188a of the rate control housing as the rate control housing is rotated. Elongated body portion 188a is also provided with a longitudinally extending bore 190 that slidably receives the rearward portion of a disabling shaft 253, the construction and operation of which will presently be described.

As illustrated in FIGS. 31, 37 and 38, body portion 188a is also provided with a longitudinally extending fluid passageway 194 that communicates with the flow passageway 178a of the previously identified piercing member 178 via the flow rate control means. For a purpose presently to be described, body portion 188a is also provided with a plurality of forwardly positioned, circumferentially spaced apart, radially extending outlet fluid flow passageways 198, 200, 202 and 204 that communicate with longitudinally extending, central passageway 194 (FIGS. 41, 42 and 43).

In a manner presently to be described, a plurality of longitudinally spaced apart, radially extending inlet fluid flow passageways 199, 201, 203 and 205 (FIG. 42) also communicate with fluid passageway 194 and as the rate control housing 188 is rotated, selectively communicate with a rate control assembly 208 (FIG. 34) that is mounted within a cavity 210 provided in a housing 180 (FIG. 37). Rate control assembly 208, which also forms a part of the flow control means of this latest form of the invention, is maintained within cavity 210 by a rate control cover 212, which also forms a part of the flow control means of the invention. As best seen in FIG. 33 of the drawings rate control cover 212 is disposed within a cavity 216 formed in housing 180.

Turning to FIGS. 34 through 36, it can be seen that rate control assembly 208 comprises a rate control plate 220, which as shown in FIG. 36 is provided with a plurality of spaced apart, serpentine micro-channels 222, 224, 226 and 228. Each of the micro-channels is of a different width, depth and length and each has an inlet in communication with an elongated passageway 230, which, in turn is in communication with the internal passageway 178a of the penetrating member 178 via a pressure regulator 231, and via passageways 232 and 234 formed in housing 180 (see FIG. 37). A thin cover 234 covers the channels in the manner shown in FIG. 34.

When assemblies 52 and 174 are interconnected in the manner shown in FIG. 32, elongated passageway 234 is in communication with penetrating member 178 via a connector collar 236 provided on rate control plate 220, via passageway 232 and via passageway 234 (FIG. 37).

In using the apparatus of the invention, the first step is to remove the sterile covers 64a and 182 from assemblies 52 and 174. This done, the assemblies can be interconnected by inserting the externally threaded neck 64 of assembly 52 into internally threaded cavity 184 of assembly 174 and rotating assembly 52 relative to assembly 174. As the assemblies are mated, penetrating member 178 will penetrate elastomeric member 78 and closure wall 72 of the container.

With communication between the fluid reservoir 74 and the internal passageway 178a of the penetrating member 178 having thusly been established, the fluid contained within the fluid reservoir can be expelled from the reservoir 74 by rotating the carriage release member 120 in the manner previously described. Once the carriage release member is free from the locking member receiving protuberance, the stored energy means, here shown as a coil spring 126 that is movable from the first compressed position to the second extended position, will urge the carriage forwardly. As the carriage moves forwardly, the accordion side walls of the container collapse causing the fluid to be forced outwardly of the reservoir into internal passageway 178a of the penetrating member. The fluid will then flow toward passageway 230 of the rate control plate 220 via the pressure regulator 231. From the pressure regulator, which controllably adjusts the pressure of the fluid flowing therefrom, the fluid will flow into and fill each of the micro-channels to 222, 224, 226 and 228 that are interconnected with passageway 230 in the manner shown in FIG. 36.

To enable the fluid to flow from the reservoir 74 to the patient via the administration set 130 (FIG. 8A) that can be connected to the outlet port 233 of housing 180 (FIG. 33), the fluid control locking means of this latest form of the invention must be operated. More particularly to permit fluid flow selectively from the outlets 222a, 224a, 226a, and 228a, respectively, of the differently configured micro-channels (FIG. 36), the rate control housing 188 must be controllably rotated in a manner to selectively align the radially extending passageways 199, 201, 203 and 205 (FIG. 39) with the longitudinally spaced apart flow passageways 237, 238, 239 and 240 formed in housing 180 (FIG. 37). Since passageways 237, 238, 239 and 240 are in communication with micro-channel outlets 222a, 224a, 226a, and 228a, respectively, of the differently configured micro-channels, fluid can flow from the selected micro-channel toward the selected flow passageway 237, 238, 239 or 240 at a controlled rate that depends upon the configuration of the particular channel selected. From the selected flow passageways 237, 238, 239 and 240, fluid will flow through one of the selected longitudinally spaced apart radially extending passageways formed in the rate control housing. From this selected passageway (shown in FIG. 39 as passageway 199) the fluid will flow into passageway 194 and then into passageway 246 formed in housing 180. From passageway 237 the fluid flows at the selected flow rate into the inlet of the administration set for delivery to the patient at the selected rate. As in the earlier described embodiment, any gases trapped in the device reservoir and in the various fluid passageways will be vented to atmosphere via a vent port 247 and passageway 247a (FIG. 33).

As in the earlier described embodiment of the invention, rotation of the rate control housing 188 cannot be accomplished until the rate control locking means is operated by the caregiver. In this latest form of the invention the rate control locking means comprises a plunger 248 that includes a locking finger 248a (FIG. 37) that prevents rotation of the rate control housing, unless and until the plunger is moved inwardly of the housing against the urging of a biasing means shown here as coil spring 251 that is housed within a chamber 254 formed in housing 180. Once the plunger is appropriately urged inwardly and removed from the channels 188d formed in flange 188b, rate control housing 188 can be rotated into the desired fluid flow position by grasping rotation fingers 188c and imparting a rotational force thereto. Referring particularly to FIGS. 37 and 42, it is to be noted that as the rate control housing is rotated, spring 251 continuously urges locking finger 248a into a selected locking channel 188d formed in flange 188b. When the locking finger is seated within a particular locking channel, one of the radially extending passageways formed in the rate control housing (here shown as passageway 199) will be locked in communication with one of the outlets of one of the plurality of micro channels formed in the rate control plate in the fluid will flow through the selected micro channel toward the patient at a selected fixed-rate. When it is desired to once again create a fluid flow toward the patient, the plunger 248 must once again be depressed and the rate control housing rotated into another position.

As in the earlier described embodiment of the invention, a reservoir viewing window 160 is provided in housing 62 so that the amount of fluid contained within reservoir 74 can be viewed. Additionally, fluid level indicia 162 are provided on housing 62, proximate window 160, so that the fluid remaining within the reservoir can be accurately monitored by the caregiver.

Fluid flow from the reservoir 74 toward the rate control assembly of the second assembly 174 via passageway 236 can be prevented through operation of the disabling means of the invention. This important disabling means, which is of a similar construction and operation to that earlier described, comprises a disabling shaft 253. As indicated in FIG. 37 of the drawings, when the disabling shaft 253 is pushed inwardly from the position shown in FIG. 37 into an inward position, wherein it resides within a cavity 255 provided in housing 188, the forward portion 253a of the disabling shaft will move into a position where it blocks fluid flow from passageway 194 toward passageway 246 so as to stop fluid flow toward the administration set. By stopping fluid flow in this manner, the apparatus is substantially disabled until the disabling shaft 253 is once again returned to the starting position shown in FIG. 37 of the drawings.

Figure 44:
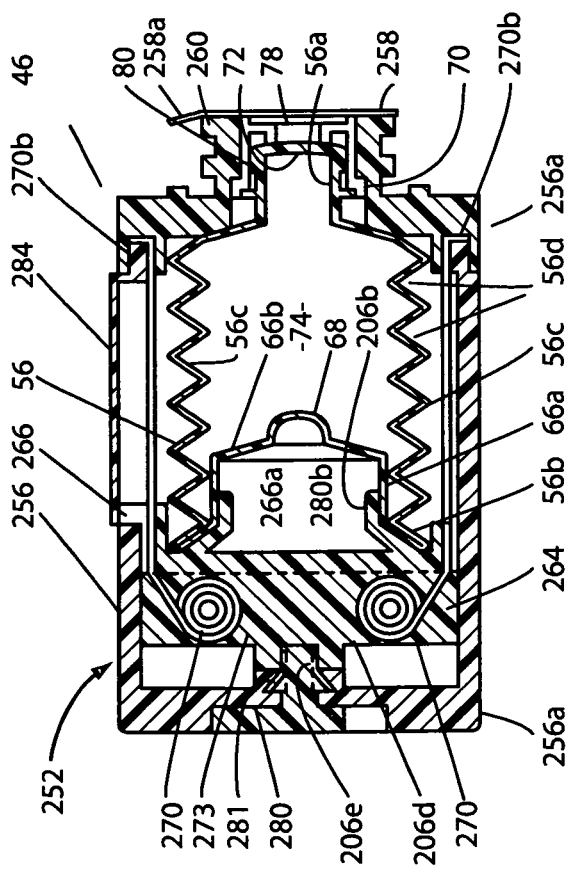
FIG. 44 is a longitudinal cross-sectional view of an alternate form of the first stand-alone component of the invention shown in FIGS. 1 and 2.
Figure 45:
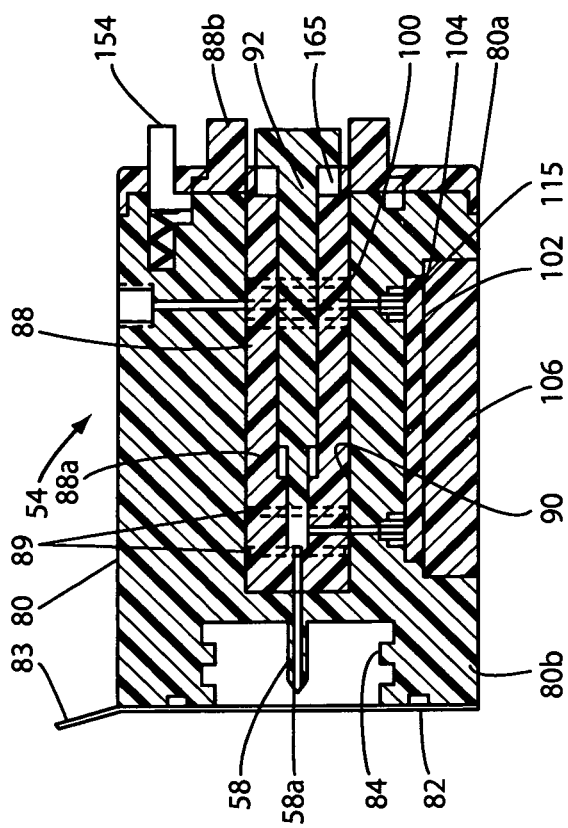
FIG. 45 is a longitudinal cross-sectional view similar to the second stand-alone component shown in FIGS. 4, 5 and 6.

Turning next to FIGS. 41 through 43, still another form of the two part fluid dispensing apparatus of the present invention for dispensing medicaments is there shown. This second, alternate, form of dispensing apparatus is similar in many respects to the earlier described embodiments of the invention and like numerals are used in FIGS. 44 through 47 to identify like components. As before, dispensing apparatus 174 comprises two stand-alone, interconnectable assemblies of the character shown in FIGS. 44 and 47. As indicated in FIG. 44, first assembly 252 is of a somewhat different construction, while second assembly 54 is substantially identical in construction and operation to the previously described second assembly 54. The primary difference between first assembly 252 and the previously described assembly 52 resides in the provision of a totally different stored energy means for moving a somewhat differently configured carriage 264 from a first retracted position to a second advanced position. Second assembly 54 includes a rate control assembly that permits the delivery of fluid to the patient at substantially a fixed rate The reservoir defining component 56 of this latest form of the invention is quite similar in construction and operation to the previously described and is constructed in accordance with aseptic blow-fill seal manufacturing techniques the character previously described. Following molding, filling and sealing the reservoir defining component is sterilized at a relatively high temperature.

In a manner presently to be described, fluid medicament reservoir 74 of the fluid reservoir assembly 252 is accessible via the penetrating member 58 of the fluid delivery and control assembly 54. More particularly, penetrating member 58 is adapted to pierce closure wall 72 as well as a pierceable membrane 78 (FIG. 44) which is positioned over closure wall 72 of by means of a closure cap 80 which is affixed to the neck portion 70 of reservoir defining assembly 56 (see FIG. 11).

Considering now in greater detail the first assembly 252 of this latest form of the fluid dispensing apparatus, this assembly comprises a generally cylindrically shaped housing 256 having a forward portion 256a and a rearward portion 256b. Forward portion 256a, which is sealed by a sterile barrier 258 having a pull tab 258a, includes an externally threaded neck 260 that is receivable within threaded cavity 84 of the second assembly 54.

In addition to the reservoir defining component 56, assembly 252 includes a carriage assembly 264 and a stored energy means that is operably associated with the carriage assembly for moving the carriage assembly between the first retracted position and the second advanced position. Carriage assembly 264 includes a base assembly 266 that includes a forward portion having, a base 266, a reservoir receiving flange 266b and a fluid level indicator boss 266c. Base assembly 266 also includes a rear portion having housing 266d that is provided with a threaded carriage locking member receiving cavity 266e (see also FIG. 47). mounted within the housing 273 is the important stored energy means of this latest form of the invention which here comprises a pair of constant force springs 270. Carriage assembly 264 is releasably locked in its first position by a novel carriage locking means, the character of which will be described in the paragraphs which follow.

As in the earlier described embodiments of the invention and as illustrated in FIG. 11 of the drawings, reservoir defining component 56 here comprises an integrally formed, hermetically sealed container that includes a front portion 56a, a rear portion 56b and a collapsible accordion-like, continuous, uninterrupted side wall 56c that interconnects the front and rear portion of the container. As illustrated in the drawings, the accordion like side wall 56c comprises a multiplicity of adjacent generally "V" shaped interconnected folds, 56d. Rear portion 56b of the container includes an inwardly extending ullage segment 66 having a side wall 66a and an end wall 66b. As illustrated in FIGS. 7 and 11, end wall 66b includes a generally hemispherical shaped protuberance 68. Front portion 56a of the container includes an integrally formed neck 70 having a closure wall 72. Front portion 56a, rear portion 56b and side wall 56c cooperate to define the fluid reservoir 74 of the fluid reservoir assembly 52.

Figure 47:
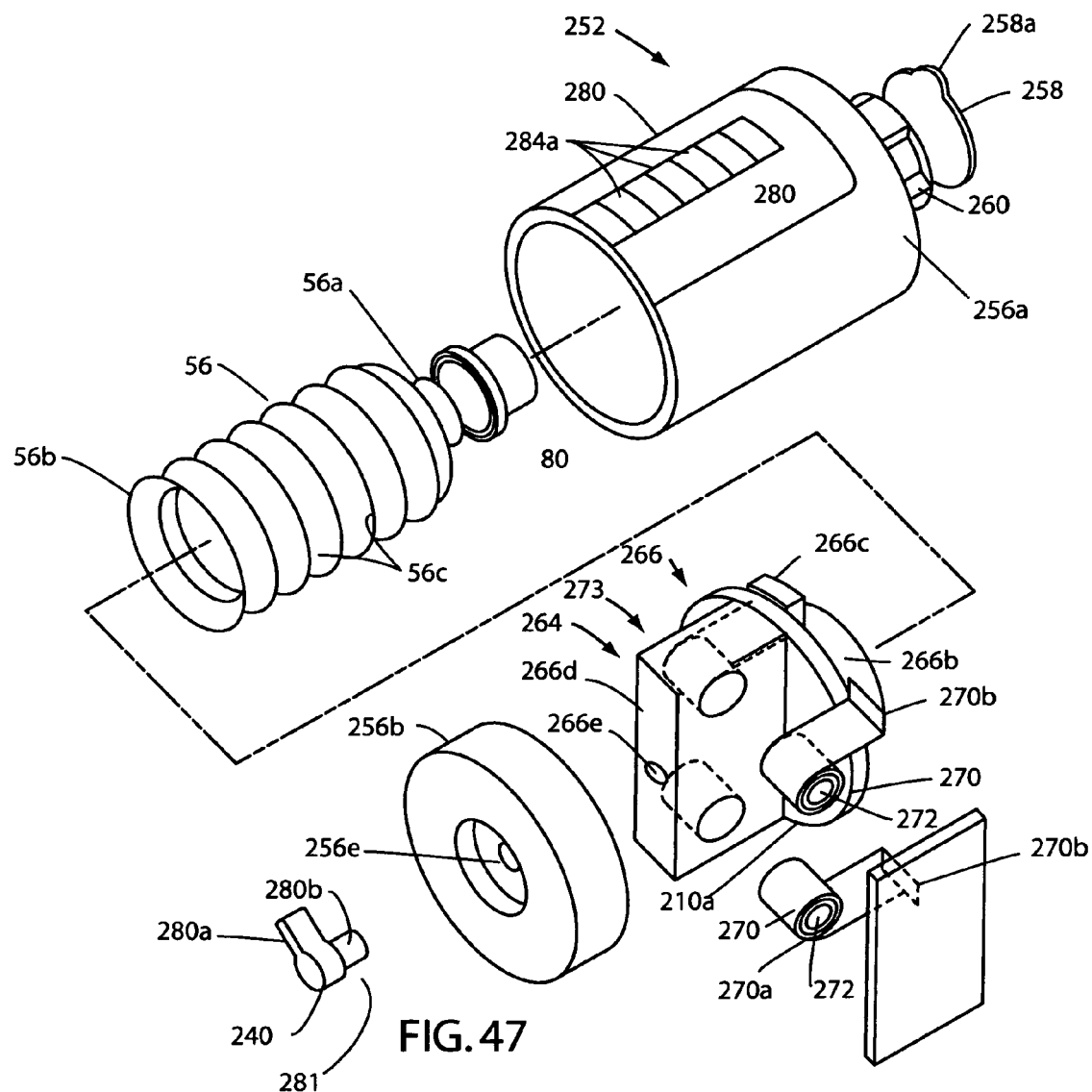
FIG. 47 is a generally perspective exploded view of the second stand-alone component of the invention shown in FIG. 17.

Constant force springs, such as springs 270 are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force, the same as a common extension spring but at a nearly constant (zero) rate. The constant-force spring is well suited to long extensions with no load build-up. As best seen in FIGS. 44 and 47, springs 270 are mounted with one end 270a tightly wrapped on a drum 272 that is housed with a carriage block 273 and the other end 270b attached forward portion 256a of housing 256 in the manner shown in FIG. 47.

In using the apparatus of this latest form of the invention, the first step is to remove the sterile covers 258 and 82 from assemblies 252 and 54. This done, the assemblies can be interconnected by inserting the externally threaded neck 260 of assembly 252 into internally threaded cavity 84 of assembly 54 and rotating assembly 252 relative to assembly 54. As the assemblies mate, penetrating member 58 will penetrate elastomeric member 78 and closure wall 72 of the container.

With communication between the fluid reservoir 74 and the internal passageway 58a of the penetrating member 58 having thusly been established, the fluid contained within the fluid reservoir can be expelled from the reservoir 74 by rotating the carriage release member 280 which comprises a part of the previously identified carriage locking means. This is accomplished by grasping the finger engaging arm 280a of the release member (FIG. 47) and rotating the member until the threaded shank 280b of the knob threadably disengages from the locking member receiving cavity 266e. Release member 280 is held in position within base 266d by means of circumferentially spaced locking tabs 281 provided on shank 280b. Once the carriage release member is free from the locking member receiving cavity, the stored energy means, here shown as constant force springs 270, will urge the carriage assembly 266 forwardly. As the carriage moves the accordion side walls 56c of the collapsible container well collapse and the fluid will be forced outwardly of the reservoir into internal passageway 58a of the penetrating member. In the manner previously described, the fluid will then flow toward the fluid flow control means of assembly 54, which functions to control the flow of fluid from the fluid reservoir of the fluid delivery portion of the device toward the patient.

To enable the fluid to flow from the reservoir 74 to the patient via the administration set 130 (FIG. 8A), the fluid control locking means must be operated in the manner previously described in connection with the first embodiment of the invention.

Referring to FIGS. 44 and 47, it is to be noted that a reservoir viewing window 284 is provided in housing 256 so that the amount of fluid contained within reservoir 74 can be determined by viewing the advance of the fluid indicator boss 266c. Additionally, fluid level indicia 284a are provided on window 284 so that the fluid remaining within the reservoir can be accurately monitored by the caregiver.

As in the earlier described embodiments of the invention, fluid flow from the reservoir 74 toward the rate control assembly of the second assembly 54 can be prevented through operation of the disabling means of the invention in a manner previously described, which disabling means comprises the previously identified disabling shaft 92.

Figure 48:
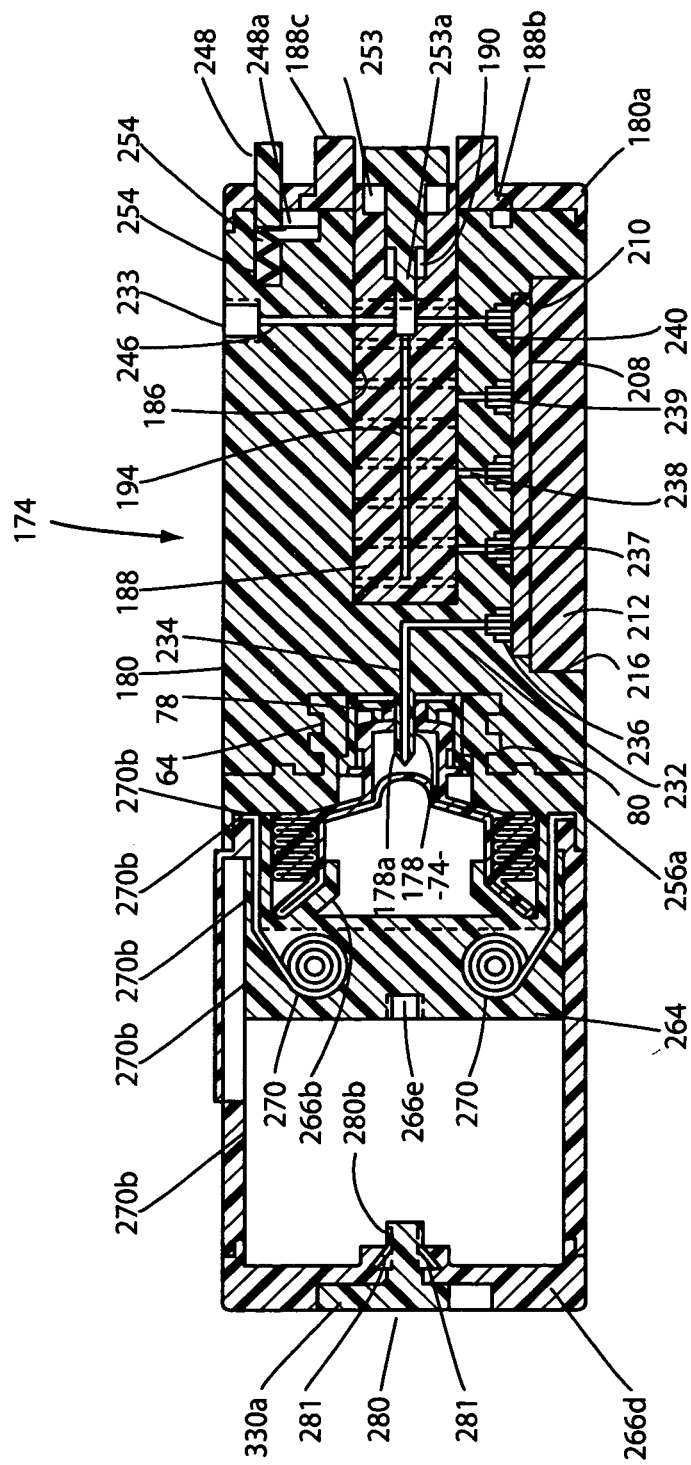
FIG. 48 is a longitudinal cross-sectional view of the fluid dispensing apparatus of the invention shown in FIG. 17 wherein the first and second stand-alone components of the invention have been irreversibly operably interconnected.

Turning to FIG. 48 yet another form of the two part fluid dispensing apparatus of the present invention for dispensing medicaments is there shown and generally identified by the numeral 290. This alternate form of dispensing apparatus is similar in many respects to the earlier described embodiments of the invention and like numerals are used to identify like components (FIG. 48). As before, dispensing apparatus 290 comprises two stand-alone, interconnectable assemblies 252 and 174. As indicated in FIG. 48, first assembly 252 is substantially identical in construction and operation to the previously described first assembly that is illustrated in FIG. 44 of the drawings and comprises a fluid reservoir assembly that houses a fluid reservoir defining component 56 that is acted upon by a pair of constant for springs 270. Assembly 174 is substantially identical in construction and operation to the previously described second assembly that is illustrated in FIGS. 31, 33 and 37 of the drawings.

Assembly 174 comprises a penetrating member 178 and a novel fluid flow control means that includes a rate control assembly that permits the delivery of fluid to the patient at a plurality of selected rates of flow.

As in the earlier described embodiments of the invention, reservoir defining component 56 is constructed in accordance with aseptic blow-fill seal manufacturing techniques. As before, following molding, filling and sealing the reservoir defining component is sterilized at a relatively high temperature.

As before, second assembly 174 of this latest form of the fluid dispensing apparatus comprises a housing 180 that includes a longitudinally extending bore 186 that rotatably receives the rate control housing 188 of the second assembly, which rate control housing forms a part of the flow control means of the invention. The flow control means includes a rate control assembly 208 that is mounted within a cavity 210 provided in housing 180. Rate control assembly 208 comprises a rate control plate 220 that is provided with a plurality of spaced apart, serpentine micro-channels, each of which is of a different width, depth and length. When assemblies 252 and 174 are interconnected in the manner shown in FIG. 48, elongated passageway 230 of the rate control plate 220 is in communication with penetrating member 178 via a connector collar 236 provided on rate control plate 220, via passageway 232 and passageway 234.

With communication between the fluid reservoir 74 and the internal passageway 178a of the penetrating member 178 established, the fluid contained within the fluid reservoir can be expelled from the reservoir 74 by rotating the carriage release member 280 in the manner previously described. Once the carriage release member is free from the locking member receiving cavity 266e, the stored energy means, here shown as the pair of constant force springs 270 will urge the carriage forwardly. As the carriage moves forwardly, the accordion side walls of the container collapse causing the fluid to be forced outwardly from the reservoir into internal passageway 178a of the penetrating member. The fluid will then flow toward passageway 230 of the rate control plate 220 via the pressure regulator 231 and then into each of the microchannels to 222, 224, 226 and 228 that are interconnected with passageway 230. To enable the fluid to flow from the reservoir 74 to the patient at a selected rate via the administration set 130, the fluid control locking means of this latest form of the invention must be operated in the manner previously described.

As in the earlier described embodiments of the invention, a reservoir viewing window 284 is provided in housing 252 so that the amount of fluid contained within reservoir 74 can be monitored. Similarly, fluid flow from the reservoir 74 toward the rate control assembly of the second assembly can be prevented through operation of the disabling means that is of the character previously described.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for dispensing medicaments to a patient comprising first and second stand-alone threadably, interconnectable assemblies, said first assembly comprising a housing having a threaded neck portion, a first removable cover covering said threaded neck portion, an integrally formed, hermetically sealed collapsible container for containing a medicinal fluid disposed within said housing, said collapsible container having a front portion, a rear portion and a collapsible accordion-like continuous uninterrupted side wall that interconnects said front and rear portions, said front portion of said collapsible container including a closure wall and a pierceable membrane positioned over said closure wall and said rear portion of said collapsible container including an inwardly extending ullage segment; and stored energy means for controllably collapsing said sealed container and said second assembly having a threaded neck portion, a second removable cover covering said threaded neck portion and including a penetrating member and housing having a longitudinally extending bore, said second, assembly further comprising a fluid delivery and control means for controlling the flow of medicinal fluid from said container of said first assembly toward the patient, said fluid and delivery and control means comprising a rate control housing rotatably mounted within said longitudinally extending bore, said rate control housing comprising an elongated body portion, a forward flange and a forwardly extending finger engaging portion connected to said flange, said elongated portion connected to said flange, said elongated body portion having a longitudinally extending fluid passageway that communicates with said piercing member and a plurality of circumferentially spaced apart, radially extending outlet fluid passageways that communicate with said longitudinally extending fluid passageway.

2. The apparatus as defined in claim 1 in which said first and second covers comprise first and second sterile barriers for sealing said first and second neck portions respectively.

3. The apparatus as defined in claim 1 in which said first assembly further includes a carriage housed within said housing of said first assembly, said carriage being operably associated with said container and with said stored energy source and being movable by said stored energy source from a first retracted position to a second advanced position.

4. The apparatus as defined in claim 1 in which said storage energy source comprises a spring.

5. The apparatus as defined in claim 1 in which said stored energy source comprises a constant force spring.

6. An apparatus for dispensing medicaments to a patient comprising first and second interconnectable assemblies, said first assembly comprising a housing having a threaded neck portion, a first removable cover covering said threaded neck portion, an integrally formed, hermetically sealed collapsible container having a reservoir for containing a medicinal fluid disposed within said housing, said collapsible container having an outlet and a front portion, a rear portion and a collapsible accordion-like continuous uninterrupted side wall that interconnects said front and rear portions, said front portion of said collapsible container including a closure wall and a pierceable membrane positioned over said closure wall and said rear portion of said collapsible container including an inwardly extending ullage segment, and stored energy means for controllably collapsing said sealed container and said second assembly including a penetrating member and a housing having an outlet, a longitudinally extending bore and a threaded neck portion, a second removable cover covering said threaded neck portion and fluid delivery and control means carried within said housing for controlling the flow of medicinal fluid from said container of said first assembly toward said outlet of said housing of said second assembly, said fluid delivery and control means comprising;
  (a) a rate control assembly, including a rate control plate having a generally planar surface provided with an inlet in communication with said outlet of said collapsible container;
  (b) a rate control housing rotatably mounted within said longitudinally extending bore, said rate control housing comprising a body portion and a forwardly extending finger engaging portion, said body portion having a longitudinally extending fluid passageway in communication with said piercing member and a plurality of longitudinally spaced apart radially extending inlet passageways in communication with said outlets of said micro-channel, said rate control housing further having a plurality of circumferentially spaced, radially extending outlet passageways in communication with said outlet of said housing of said second assembly; and
  (c) a fluid control locking means for preventing rotation of said rate control housing.

7. The apparatus as defined in claim 6 in which said first assembly further includes a carriage housed within said housing of said first assembly, said carriage being operably associated with said container and with said stored energy source and being movable by said stored energy source from a first retracted position to a second advanced position.

8. The apparatus as defined in claim 6 in which said storage energy source comprises a constant force spring.

9. The apparatus as defined in claim 6 in which said housing of said first assembly is provided with a viewing window for viewing said fluid reservoir.

10. A two part apparatus for dispensing medicaments to a patient comprising:
  (a) a first stand-alone assembly comprising a housing having a threaded neck portion, an integrally formed, hermetically sealed collapsible container for containing a medicinal fluid disposed within said housing and a spring operably associated with said collapsible container for controllably collapsing said collapsible container, said collapsible container including a front portion, a rear portion and a collapsible accordion-like, continuous, uninterrupted side wall that interconnects said front and rear portions, said front portion of said collapsible container including a closure wall and a pierceable membrane positioned over said closure wall and said rear portion of said collapsible container including an inwardly extending ullage segment; and
  (b) a second stand-alone assembly threadably interconnectable with said first assembly, said second assembly including:
    (i) a housing having a threaded neck receiving portion for receiving the threaded neck portion of said first assembly;
    (ii) fluid delivery and control means carried by said housing of said second assembly for controlling the flow of medicinal fluid from said container of said first assembly toward the patient, said fluid delivery and control means comprising:
      a. a rotatable rate control housing having a body portion having a longitudinally extending bore, a flange portion having a plurality of circumferentially spaced apart cavities; and
      b. a fluid control locking means for preventing rotation of said rate control housing, said fluid control locking means comprising a plunger received within said longitudinally extending bore, said plunger having a locking finger receivable within said spaced apart cavities of said flange portion of said body portion of said rate control housing.

11. The apparatus as defined in claim 1 in which said elongated body portion of said rate control housing includes a longitudinally extending bore and in which said flange portion is provided with a plurality of circumferentially spaced apart cavities, said apparatus further including fluid control locking means for preventing rotation of said rate control housing, said fluid control locking means comprising a plunger received within said longitudinally extending bore, said plunger having a locking finger receivable within said spaced apart cavities of said flange portion of said body portion of said rate control housing.

12. The apparatus as defined in claim 6 in which said rate control housing further includes a forward flange having a plurality of circumferentially spaced cavities and in which said fluid control locking means comprises a plunger having a locking finger receivable within a selected one of said plurality of circumferentially spaced cavities.

\* \* \* \* \*